(12) United States Patent
Steiner et al.

(10) Patent No.: US 9,289,412 B2
(45) Date of Patent: Mar. 22, 2016

(54) ROLE OF LIMONOID COMPOUNDS AS NEUROPROTECTIVE AGENTS

(75) Inventors: Joseph P. Steiner, Baltimore, MD (US); Avindra Nath, Ellicott City, MD (US); Norman Haughey, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 319 days.

(21) Appl. No.: 12/590,270

(22) Filed: Nov. 5, 2009

(65) Prior Publication Data

US 2010/0056617 A1 Mar. 4, 2010

Related U.S. Application Data

(62) Division of application No. 11/893,100, filed on Aug. 13, 2007, now abandoned.

(60) Provisional application No. 60/837,365, filed on Aug. 11, 2006.

(51) Int. Cl.
A61K 31/366 (2006.01)

(52) U.S. Cl.
CPC .................................. A61K 31/366 (2013.01)

(58) Field of Classification Search
None
See application file for complete search history.

(56) References Cited

U.S. PATENT DOCUMENTS 5,589,182 A 12/1996 Tashiro et al.

FOREIGN PATENT DOCUMENTS

| WO | WO-01/32160 A2 | 5/2001 |
| WO | WO-02/055071 A1 | 7/2002 |
| WO | WO-2006/024545 A1 | 3/2006 |
| WO | WO-2008/151833 A2 | 12/2008 |
| WO | WO-2009/020601 A2 | 2/2009 |

OTHER PUBLICATIONS

Sacktor et al. Novel markers of oxidative stress in actively progressive HIV dementia. Journal of Neuroimmunology, 157, 2004, 176-184.*
Turchan et al. Neuroprotective therapy for HIV dementia. Current HIV Research, 2003, I, 373-383.*

(Continued)

*Primary Examiner* — Anna Pagonakis
(74) *Attorney, Agent, or Firm* — Mintz Levin Cohn Ferris Glovsky and Popeo, P.C.; Peter F. Corless; Christopher R. Cowles

(57) ABSTRACT

Disclosed herein are neuroprotective compounds. Methods for the preparation of such compounds are disclosed. Also disclosed are pharmaceutical compositions that include the compounds. Methods of using the compounds disclosed, alone or in combination with other therapeutic agents, for the treatment of neurodegenerative conditions are provided.

2 Claims, 9 Drawing Sheets

(56) References Cited

OTHER PUBLICATIONS

Kaul et al. Pathways to neuronal injury and apoptosis in HIV-associated dementia. Nature, vol. 40, Apr. 19, 2001, pp. 988-994.*

Brandt et al. Gedunin, a novel Hsp90 inhibitor: semsynthesis of derivatives and preliminary structure-activity relationship. J. Med. Chem. 2008, 51, 6495-6502.*

Toscano et al. Gedunin, a d-seco limonoid. Journal of Chemical Crystallography, vol. 26, No. 10, 1996, pp. 707-711.*

Kim et al. Effects of naturally occurring compounds on fibril formation and oxidative stress of beta-amyloid. J. Agric. Food. Chem. 2005, 53, 8537-8541.*

Lamb J. et al. "The connectivity map: using gene-expression signatures to connect small molecules, genes and disease" Science vol. 313, Sep. 29, 2006.

MacKinnon S et al. "Antimalarial activity of tropical Meliaceae extracts and gedunin derivatives." J Nat Prod. Apr. 1997;60(4):336-41.

Omar S. et al. "Traditionally-used antimalarials from the Meliaceae." Curr Top Med Chem. 2003;3(2):133-9.

International Search Report issued for PCT/US07/18001 on Apr. 10, 2008, mailed May 2, 2008.

\* cited by examiner

Khivorin

Gedunin

Odoratone

Angolensic Acid, methyl ester

Limonin

ROLE OF LIMONOID COMPOUNDS AS NEUROPROTECTIVE AGENTS

RELATED APPLICATIONS

This application is a divisional application of U.S. patent application Ser. No. 11/893,100, filed Aug. 13, 2007, which claims the benefit of U.S. Provisional Application No. 60/837,365, entitled "Role of Liminoid Compounds as Neuroprotective Agents," filed Aug. 11, 2006, the contents of each of the aforementioned documents is hereby incorporated by reference in their entirety.

BACKGROUND OF THE INVENTION

Neurodegenerative conditions such as Alzheimer's Disease, multiple sclerosis, AIDS-related dementia, Huntington's Disease, stroke, and spinal cord trauma are characterized by extensive loss of neurons or glia.

SUMMARY OF THE INVENTION

Described herein are neuroprotective compounds. Also described herein are pharmaceutical formulations comprising such neuroprotective compounds, and methods for using such neuroprotective compounds in the prophylaxis and treatment of neurodegenerative conditions.

Accordingly, in one aspect provided herein is a pharmaceutical composition comprising at least one compound having the structure of Formula I:

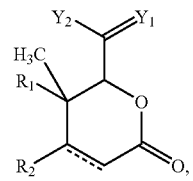

wherein each compound of Formula I is in a substantially purified form; and $Y_1$ is O and $Y_2$ is OH, O-alkyl, O-(hydroxyalkyl) or O-(alkoxyalkyl); or $Y_1$ and $Y_2$ together form a furan group;

$R_1$ and $R_2$ together form a substituted cycloalkyl or cycloalkenyl group; and ------ is selected from ═══ ,

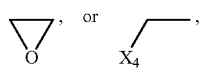

wherein $X_4$ and $R_2$ together form a substituted heteroalicyclic group provided that $R_1$ is H; or pharmaceutically acceptable salts, esters, prodrugs, or metabolites thereof;

or ester derivatives, saccharide derivatives, or —(CH$_2$CH$_2$O)$_n$CH$_3$ derivatives thereof, where n is 1 to 100;

and a pharmaceutically acceptable excipient.

In a further embodiment, the at least one compound of Formula I has a structure selected from:

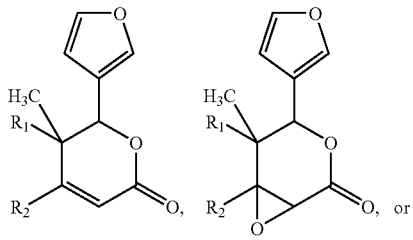

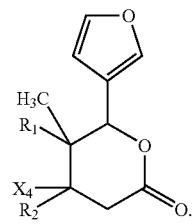

In a further embodiment, the at least one compound of Formula I has the structure:

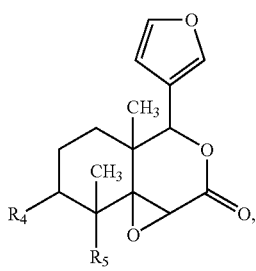

wherein $R_4$ and $R_5$ together form a substituted cycloalkyl or cycloalkenyl group.

In a further embodiment, the at least one compound of Formula I has the structure:

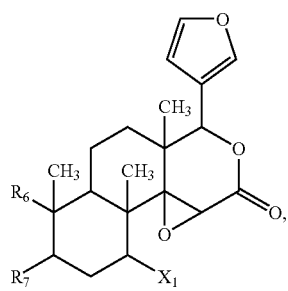

wherein $R_4$ and $R_7$ together form a substituted cycloalkyl or cycloalkenyl group; and $X_1$ is selected from H, oxo, OH, O-alkyl, O-(hydroxyalkyl), O-(alkoxyalkyl), or O—C(O)-alkyl.

In a further embodiment, the at least one compound of Formula I has a structure selected from:

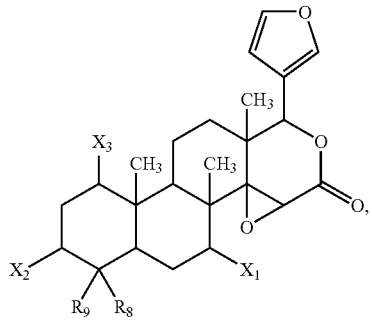

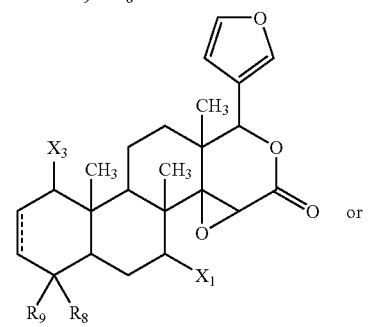

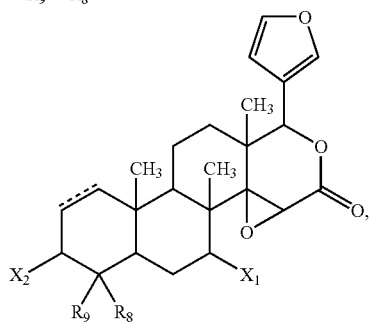

wherein $R_8$ and $R_9$ are independently H or alkyl;
$X_2$ and $X_3$ are independently selected from H, oxo, OH, O-alkyl, O-(hydroxyalkyl), O-(alkoxyalkyl), or O—C(O)-alkyl; and
------ is selected from ===== or

In a further embodiment, the at least one compound of Formula I has the structure:

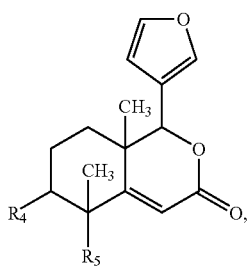

wherein $R_4$ and $R_5$ together form a substituted cycloalkyl or cycloalkenyl group.

In a further embodiment, the at least one compound of Formula I has the structure:

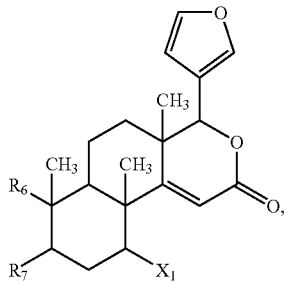

wherein $R_6$ and $R_7$ together form a substituted cycloalkyl or cycloalkenyl group; and
$X_1$ is selected from H, oxo, OH, O-alkyl, O-(hydroxyalkyl), O-(alkoxyalkyl), or O—C(O)-alkyl.

In a further embodiment, the at least one compound of Formula I has a structure selected from:

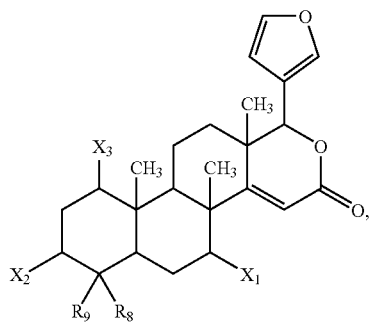

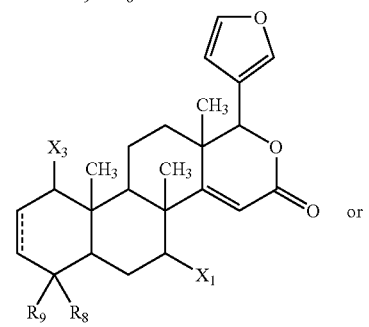

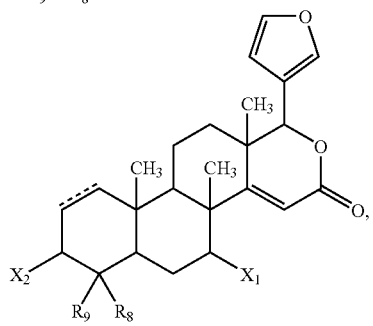

wherein $R_8$ and $R_9$ are independently H or alkyl;
$X_2$ and $X_3$ are independently selected from H, oxo, OH, O-alkyl, O-(hydroxyalkyl), O-(alkoxyalkyl), or O—C(O)-alkyl; and ------ is selected from ===== or

In a further embodiment, the at least one compound of Formula I has the structure:

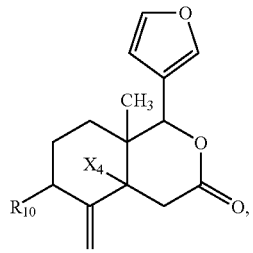

$X_4$ and $R_{10}$ together form a substituted heteroalicyclic group.

In a further embodiment, the at least one compound of Formula I has the structure:

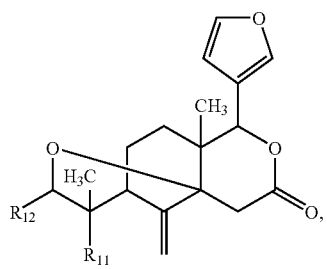

wherein $R_{11}$ and $R_{12}$ together form a substituted cycloalkyl or cycloalkenyl group.

In a further embodiment, the at least one compound of Formula I has the structure:

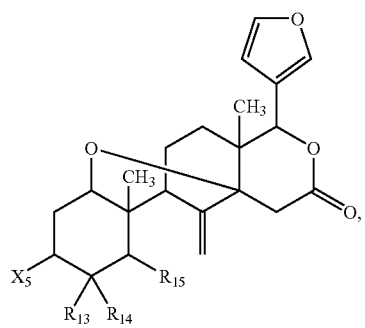

wherein $R_{13}$ and $R_{14}$ are independently H or alkyl;
$X_5$ is selected from H, oxo, OH, O-alkyl, O-(hydroxyalkyl), O-(alkoxyalkyl), or O—C(O)-alkyl; and
$R_{15}$ is alkyl-C(O)O-alkyl.

In another aspect provided herein is a pharmaceutical composition comprising at least one compound having the structure of Formula II:

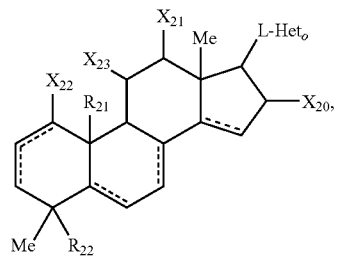

wherein $Het_O$ is a substituted or unsubstituted oxygen-containing aromatic or non-aromatic heterocycle; L is a bond or an alkylene group;

each ------ is independently selected from =====,

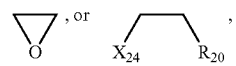

provided that no two adjacent ------ groups are adjacent ===== or

groups;

each $X_{20}$, $X_{21}$, $X_{22}$, $X_{23}$, and $X_{24}$ is independently selected from H, oxo, OH, OC(O)-alkyl, O-(hydroxyalkyl), O-(alkoxyalkyl), or O-alkyl;

each $R_{20}$, $R_{21}$ and $R_{22}$ is selected from H or alkyl; or any two of $X_{20}$, $X_{21}$, $X_{22}$, $X_{23}$, $X_{24}$, $R_{20}$, $R_{21}$, or $R_{22}$ can form an optionally substituted oxygen-containing heterocycle; or pharmaceutically acceptable salts, esters, prodrugs, or metabolites thereof;

or ester derivatives, saccharide derivatives, or —(CH$_2$CH$_2$O)$_n$CH$_3$ derivatives thereof, where n is 1 to 100;

and a pharmaceutically acceptable excipient.

In a further embodiment, the $Het_O$ is an unsubstituted furanyl group. In a further or alternative embodiment, L is a bond.

In a further or alternative embodiment, $R_{21}$ and $R_{22}$ are CH$_3$. In a further embodiment at least one of ------ groups is a =====. In a further or alternative embodiment, at least one of ------ groups is a

In a further or alternative embodiment, at least one of ------ groups is a

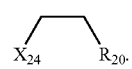

In a further or alternative embodiment, $X_{20}$ is an oxo group. In a further or alternative embodiment, the compound of Formula II is selected from:

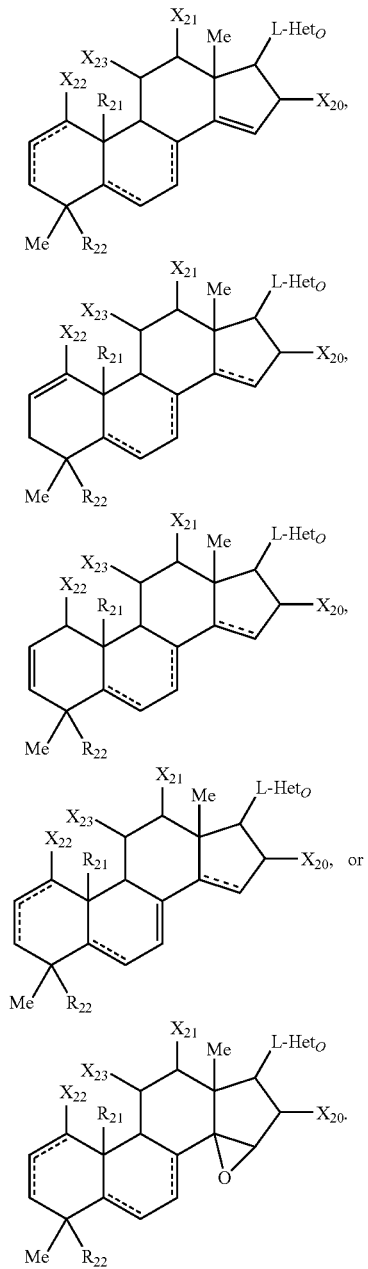

In a further or alternative embodiment, the pharmaceutical composition has a therapeutically effective amount of a compound presented in Tables 2 or 3, along with pharmaceutically acceptable excipients. In a further or alternative embodiment, the pharmaceutical composition has a therapeutically effective amount of a compound isolated from the plant families of order Rutales, including in Maliaceae and Rutaceae. In a further or alternative embodiment, the pharmaceutical composition has a therapeutically effective amount of a compound derived from a 4,4,8-trimethyl-17-furanylsteroid skeleton. In a further or alternative embodiment, the pharmaceutical composition has a therapeutically effective amount of a compound is a tetranortriterpenoid.

In another aspect provided herein is a method for treating or reducing the risk of a neurodegenerative condition in a subject in need thereof by administering to the subject a therapeutically effective amount of any of the above-described neuroprotective compound compositions. In some embodiments, the sole active ingredient in the pharmaceutical composition administered to the subject is a neuroprotective compound disclosed herein. In some embodiments, the composition to be administered to the subject comprises a neuroprotective compound that at a concentration of 10 µM provides at least 6% (e.g., at least 20%, 50%, or 70%) protection against 3 mM 3-nitropropionic acid to rat mixed hippocampal cultures. In some embodiments, the subject is diagnosed as suffering from the neurodegenerative condition prior to administration of the composition. In some embodiments, administration of the composition to the subject is parenteral, intravenous, subcutaneous, intra-muscular, transnasal, intra-arterial, transdermal, or respiratory. In some embodiments, the subject to be treated is administered, in addition to one of the above-described compositions, a composition comprising a therapeutically effective amount of a polyphenol (e.g., resveratrol or epigallocatechin 3-gallate) or an antioxidant compound (e.g., Vitamin C or Vitamin E).

In a related aspect, the subject to be treated is suffering from a chronic neurodegenerative condition. In some embodiments, the chronic neurodegenerative condition is Alzheimer's disease. In some embodiments, in addition to administering one of the above-described neuroprotective compositions to a subject suffering from Alzheimer's Disease, the level of one or more Alzheimer's Disease prognostic biomarkers is determined in a biological sample from the subject. In some embodiments, one or more Alzheimer's Disease prognostic biomarkers to be assayed comprise tau protein, phospho-tau protein, $\beta$-amyloid$_{1-42}$ peptide, $\beta$-amyloid$_{1-40}$ peptide, C1q protein, IL-6 protein, ApoE protein, $\alpha$-1-antichymotrypsin protein, oxysterol, isoprostane, 3-nitrotyrosine, or any combination thereof. In some embodiments, the subject to be treated is suffering from multiple sclerosis. In some embodiments, the subject to be treated is suffering from Huntington's disease. In some embodiments, the subject to be treated is suffering from AIDS-related dementia. In some embodiments, the subject to be treated is suffering from schizophrenia. In some embodiments, the subject to be treated is suffering from Amyotrophic Lateral Sclerosis. In some embodiments, the subject to be treated is suffering from a retinal disease. In some embodiments, the subject to be treated is suffering from glaucoma, optic neuritis, compressive optic neuropathy, or a hereditary neuropathy. In some embodiments, the subject to be treated is suffering from epilepsy.

In a related aspect, the subject to be treated is suffering from an acute neurodegenerative condition. In some embodiments, the subject to be treated is suffering from a stroke (e.g., an acute thromboembolic stroke, a focal ischemia, a global ischemia, or a transient ischemic attack). In some embodiments, the subject to be treated is suffering from ischemia resulting from a surgical technique involving prolonged halt of blood flow to the brain. In some embodiments, the subject to be treated is suffering from head trauma. In some embodiments, the subject to be treated is suffering from spinal trauma. In some embodiments, the subject to be treated is suffering from an optic nerve stroke, anterior ischemic optic neuropathy, or traumatic optic neuropathy.

In another aspect provided herein is a method for treating multiple sclerosis in a subject in need thereof by administering to the subject a therapeutically effective amount of any of the above-described neuroprotective compound compositions.

In a further aspect provided herein is a method for treating AIDS-related dementia in a subject in need thereof by administering to the subject a therapeutically effective amount of any of the above-described neuroprotective compound compositions.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Figure 1:
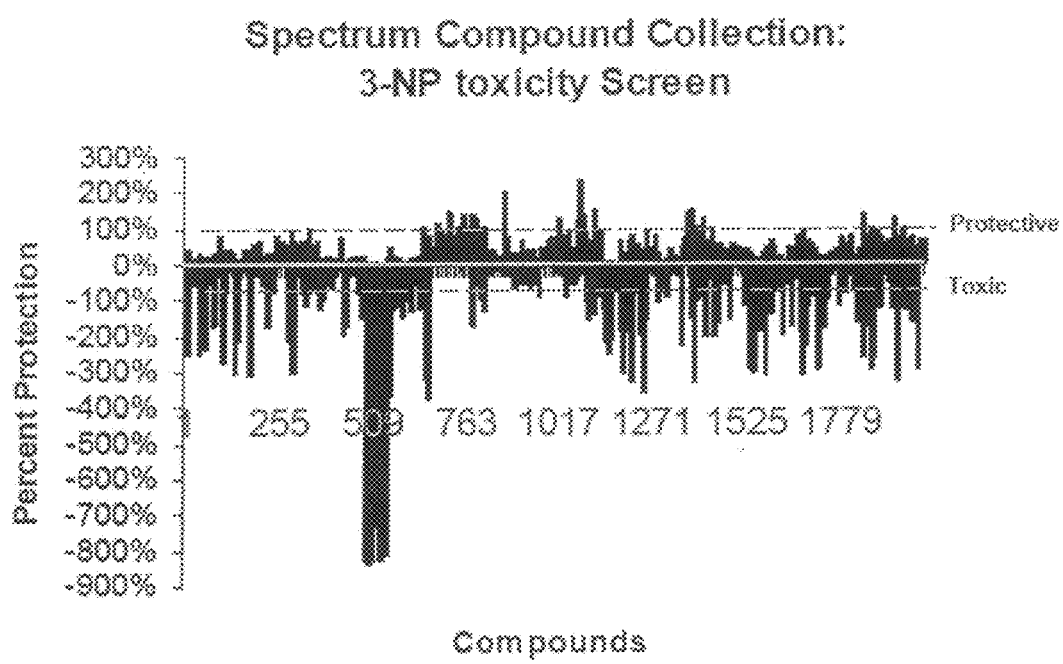
FIG. 1 is a bar graph showing the results of an in vitro screen for neuroprotective compounds performed on a library of compounds (Spectrum Collection from MicroSource Discovery Systems, Inc.) containing FDA approved compounds, natural products, and other bioactive compounds.

The appended claims particularly point out features set forth herein. A better understanding of the features and advantages of the present disclosure will be obtained by reference to the following detailed description that sets forth illustrative embodiments, in which the principles described herein are utilized.

Disclosed herein are neuroprotective compounds that decrease induced or spontaneous neuronal or glial cell death, compositions that include the neuroprotective compounds, and methods of their use in treating a neurodegenerative condition. The neuroprotective compounds described herein are shown to promote survival of neurons and glia in response to cytotoxic challenges, e.g., oxidative stress. Cytotoxic challenges are associated with a number of neurodegenerative conditions (see, e.g., Lin et al. (2006), *Nature,* 443(7113): 787-795); contact with neurotoxic viral proteins such as HIV Tat (see King et al. (2006), *Microbes Infect* 2006, 8(5): 1347-1357); and hypoxia (see Won et al. (2002), *J Biochem Mol Biol* 2002, 35(1):67-86). Accordingly, the neuroprotective compounds, compositions, methods described herein can be used to treat a variety of neurodegenerative conditions.

In some embodiments, the methods described herein are used to treat a chronic neurodegenerative disease, which includes, but is not limited to, Alzheimer's Disease, Multiple Sclerosis, HIV-associated dementia, Schizophrenia, Huntington's Disease, Parkinson's Disease, Amyotrophic Lateral Sclerosis, Multiple System Atrophy, degenerative retinal disease (e.g., macular degeneration), optic neuropathies (e.g., glaucoma, optic nerve stroke, optic neuritis, anterior ischemic optic neuropathy, traumatic optic neuropathy, compressive optic neuropathy, or hereditary neuropathies, such as Leber's hereditary optic neuropathy), Schizophrenia, Pick's disease, Alexander disease, Alper's disease, Ataxia telangiectasia, Batten disease (also known as Spielmeyer-Vogt-Sjogren-Batten disease), Canavan disease, Cockayne syndrome, Corticobasal degeneration, Creutzfeldt-Jakob disease, Kennedy's disease, Krabbe disease, Lewy body dementia, Machado-Joseph disease (Spinocerebellar ataxia type 3), Neuroborreliosis, Pelizaeus-Merzbacher Disease, Primary lateral sclerosis, Prion diseases, Refsum's disease, Sandhoff disease, Schilder's disease, Spielmeyer-Vogt-Sjogren-Batten disease (also known as Batten disease), Spinocerebellar ataxia (multiple types with varying characteristics), Spinal muscular atrophy, Steele-Richardson-Olszewsli disease, Tabes dorsalis, or any combination thereof.

In some embodiments, the methods described herein can be used to treat acute neurodegenerative conditions, which include, but are not limited to stroke (e.g., thromboembolic stroke, focal ischemia, global ischemia, or transient ischemic attack), ischemia resulting from a surgical technique involving prolonged halt of blood flow to the brain, head trauma, spinal trauma, or any combination thereof.

Symptoms, diagnostic tests, and prognostic tests for each of the above-mentioned conditions are described in, e.g., the *Diagnostic and Statistical Manual of Mental Disorders,* 4th ed., 1994, Am. Psych. Assoc.; and *Harrison's Principles of Internal Medicine©,"* 16th ed., 2004, The McGraw-Hill Companies, Inc.

For example, where the subject is at risk of or is suffering from multiple sclerosis, a set of standard criteria, such as the "McDonald Criteria" can be used for prognosis/diagnosis.

See McDonald et al. (2001), *Ann Neurol,* 50(1):121-127. Magnetic resonance imaging (MM) of the brain and spine can be used to evaluate individuals with suspected multiple sclerosis. MRI shows areas of demyelination as bright lesions on T2-weighted images or FLAIR (fluid attenuated inversion recovery) sequences. Gadolinium contrast is used to demonstrate active plaques on T1-weighted images. Further, a prognostic biomarker assay of cerebrospinal fluid (CSF) obtained by lumbar puncture can provide evidence of chronic inflammation of the central nervous system. Specifically, CSF is tested for oligoclonal bands, which are immunoglobulins found in 85% to 95% of people with definite MS, albeit not exclusively in MS patients. Additional criteria for diagnosis 3-nitrotyrosine, homocysteine, or cholesterol, or any combination thereof, e.g., the ratio of $\beta$-amyloid$_{1-42}$ peptide to $\beta$-amyloid$_{1-40}$ peptide.

The type of biological sample utilized in prognostic Alzheimer's biomarker assays will vary depending on the prognostic biomarker to be measured. Further, the relationship between the level of a prognostic biomarker and Alzheimer's risk varies depending on the particular biomarker, as well as on the biological sample in which the level of the biomarker is determined. In other words, the level of the biomarker in a biological sample may be directly correlated or inversely correlated with the risk of Alzheimer's Disease, as summarized in Table 1.

TABLE 1

ALZHEIMER'S DISEASE PROGNOSTIC BIOMARKERS

| Biomarker | Biological Sample Type | Correlation to Dementia Risk | Reference |
|---|---|---|---|
| tau protein | cerebrospinal fluid (CSF) | increased | Hampel et al. (2004), Mol Psychiatry, 9: 705-710 |
| phospho-tau protein | CSF | increased | Hampel et al. (2004), Arch Gen Psychiatry, 61: 95-102 Hansson et al. (2006), Lancet Neural, 5(3): 228-234 |
| $\beta$-amyloid$_{1-42}$ peptide | CSF | decreased | Hampel et al. (2004), Mol Psychiatry, 9: 705-710 |
| Ratio of $\beta$-amyloid$_{1-42}$ peptide to $\beta$-amyloid$_{1-40}$ peptide | plasma CSF | decreased decreased | Graff-Radford et al. (2007), Arch Neural, 64(3): 354-362; Hansson et al. (2007), Dement Geriatr Cogn Disord, 23(5): 316-20 |
| C1q protein | CSF | decreased | Smyth et al. (1994), Neurobiol Aging, 15(5): 609-614 |
| IL-6 protein | plasma CSF | increased increased | Licastro et al. (2000), J Neuroimmunol, 103: 97-102; Sun et al. (2003), Dement Geriatr Cogn Disord, 16(3): 136-44 |
| APOE protein | CSF | increased | Fukuyama et al. (2000), Eur Neural, 43(3): 161-169 |
| $\alpha$-1-antichymotrypsin protein | plasma | increased | Dik et al. (2005), Neurology, 64(8): 1371-1377. |
| oxysterol | CSF | increased | Papassotiropoulos et al. (2002), J Psychiatr Res, 36(1): 27-32 |
| isoprostane | CSF | increased | Montine et al. (2005), Antioxid Redox Signal, 7(1-2): 269-275 |
| 3-nitrotyrosine | CSF | increased | Tohgi et al. (1999), Neurosci Lett, 269(1): 52-54 |
| homocysteine | plasma | increased | Seshadri et al. (2002), N Engl J Med, 346(7): 476-83 |
| cholesterol | plasma | increased | Panza et al. (2006), Neurobiol Aging, 27(7): 933-940 | of multiple sclerosis include, e.g., a reduction in visual evoked potentials and somatosensory evoked potentials, which are indicative of demyelination.

Where a neurodegenerative disorder affects a cognitive ability, a subject can be diagnosed by any one of a number of standardized cognitive assays, e.g., the Mini-Mental State Examination, the Blessed Information Memory Concentration assay, or the Functional Activity Questionnaire. See, e.g., Adelman et al. (2005), *Am. Family Physician,* 71(9): 1745-1750. Indeed, in some cases a subject can also be diagnosed as having a high risk of developing a chronic neurodegenerative condition (e.g., Alzheimer's disease), even in the absence of overt symptoms. For example, the risk of Alzheimer's disease in a subject can be determined by detecting a decrease in the volumes of the subject's hippocampus and amygdala, using magnetic resonance imaging. See, e.g., den Heijer et al. (2006), *Arch Gen Psychiatry,* 63(1):57-62. Assay of prognostic biomarkers in a sample from a subject are also useful in prognosis or diagnosis of a chronic neurodegenerative condition. For example, where the chronic neurodegenerative condition is Alzheimer's disease, prognostic biomarkers include, but are not limited to, total tau protein, phospho-tau protein, $\beta$-amyloid$_{1-42}$ peptide, $\beta$-amyloid$_{1-40}$ peptide, complement component 1, q subcomponent (C1q) protein, interleukin 6 (IL-6) protein, apolipoprotein E (APOE) protein, $\alpha$-1-antichymotrypsin protein, oxysterol (e.g., 24S-hydroxycholesterol), isoprostane (e.g., an F2-isoprostane), Animal models are useful for establishing a range of therapeutically effective doses of neuroprotective compounds for treating any of the foregoing diseases. For example, animal models of chronic neurodegenerative conditions have been established, e.g., for Alzheimer's disease, multiple sclerosis, amyotrophic lateral sclerosis, multiple system atrophy, and Huntington's disease. See, e.g., Spires et al. (2005), *NeuroRx.,* 2(3):447-464; Gold et al. (2006), Brain, 129(8):1953-1971; Wong et al. (2002), *Nat. Neurosci.,* 5(7):633-639, Stefanova et al. (2005), *Am J Pathol,* 166(3): 869-876, Tadros et al. (2005), *Pharmacol Biochem Behav;* 82(3):574-582. These animal models develop a chronic neurodegenerative condition that is manifested behaviorally by impaired learning, memory, or locomotion. Cognitive abilities, as well as motor functions in non-human animals suffering from a chronic neurodegenerative condition can be assessed using a number of behavioral tasks. Well-established sensitive learning and memory assays include the Morris Water Maze (MWM), context-dependent fear conditioning, cued-fear conditioning, and context-dependent discrimination. See, e.g., Anger (1991), *Neurotoxicology,* 12(3):403-413. Locomotor behavior, e.g., following spinal trauma, is commonly assessed using a 21-point open field locomotion score assay developed by Basso, Beattie, and Bresnahan (BBB) (Basso, et al. (1995), *J. Neurotrauma,* 12(1): 1-21). Such animal models are suitable for testing effective dose ranges for the neuroprotective compounds and compositions described herein as well as for identifying additional neuroprotective compounds.

Certain Chemical Terminology

All patents, patent applications, published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information can be found by searching the internet. Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definition of standard chemistry terms may be found in reference works, including Carey and Sundberg "ADVANCED ORGANIC CHEMISTRY 4$^{TH}$ ED." Vols. A (2000) and B (2001), Plenum Press, New York Unless otherwise indicated, methods of mass spectroscopy, NMR, HPLC, protein chemistry, biochemistry, recombinant DNA techniques and pharmacology are employed. Standard techniques can be used for chemical syntheses, chemical analyses, pharmaceutical preparation, formulation, and delivery, and treatment of patients. Standard techniques can be used for recombinant DNA, oligonucleotide synthesis, and tissue culture and transformation (e.g., electroporation, lipofection).

As used herein, $C_1$-$C_x$ includes $C_1$-$C_2$, $C_1$-$C_3$ ... $C_1$-$C_x$.

An "alkyl" group refers to a straight-chained, branched or cyclic aliphatic hydrocarbon group. The "allyl" moiety may have 1 to 10 carbon atoms (whenever it appears herein, a numerical range such as "1 to 10" refers to each integer in the given range; e.g., "1 to 10 carbon atoms" means that the alkyl group may have 1 carbon atom, 2 carbon atoms, 3 carbon atoms, etc., up to and including 10 carbon atoms, although the present definition also covers the occurrence of the term "alkyl" where no numerical range is designated). The alkyl group of the compounds described herein may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from among methyl, ethyl, propyl; iso-propyl, n-butyl, iso-butyl, sec-butyl, and t-butyl. Thus $C_1$-$C_4$ alkyl includes $C_1$-$C_2$ alkyl and $C_1$-$C_3$ alkyl. Alkyl groups can be substituted or unsubstituted. Typical alkyl groups include, but are in no way limited to, methyl, ethyl, propyl, isopropyl, butyl, isobutyl, tertiary butyl, pentyl, hexyl, cyclopropyl, cyclobutyl, cyclopentyl, cyclohexyl, and the like.

An "alkoxy" group refers to a (alkyl)O— group, where alkyl is as defined herein.

"Hydroxyalkyl" refers to an alkyl radical, as defined herein, substituted with at least one hydroxy group. Non-limiting examples of a hydroxyalkyl include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, 2-hydroxyethyl, 2,3-dihydroxypropyl, and 1-(hydroxymethyl)-2-hydroxyethyl.

"Alkoxyalkyl" refers to an alkyl radical, as defined herein, substituted with at least one alkoxy group, as defined herein.

An "amide" is a chemical moiety with the formula —C(O)NHR or —NHC(O)R, where R is selected from among alkyl, cycloalkyl, aryl, heteroaryl (bonded through a ring carbon) and heteroalicyclic (bonded through a ring carbon). An amide moiety may form a linkage between an amino acid or a peptide molecule and a compound described herein, thereby forming a prodrug. Any amine, or carboxyl side chain on the compounds described herein can be amidified. The procedures and specific groups to make such amides can be found in Greene and Wuts, Protective Groups in Organic Synthesis, 3$^{rd}$ Ed., John Wiley & Sons, New York, N.Y., 1999, which is incorporated herein by reference in its entirety.

The term "bond" or "single bond" refers to a chemical bond between two atoms, or two moieties when the atoms joined by the bond are considered to be part of larger substructure.

The term "carbocyclic" or "carbocycle" refers to a compound which contains one or more covalently closed ring structures, and that the atoms forming the backbone of the ring are all carbon atoms. The term thus distinguishes carbocyclic from heterocyclic rings in which the ring backbone contains at least one atom which is different from carbon. Carbocycles include cycloalkyls and aryls.

The term "cycloalkyl" refers to a monocyclic or polycyclic radical that contains only carbon and hydrogen, and may be saturated, partially unsaturated, or fully unsaturated. Cycloalkyl groups include groups having from 3 to 10 ring atoms. Illustrative examples of cycloalkyl groups include the following moieties:

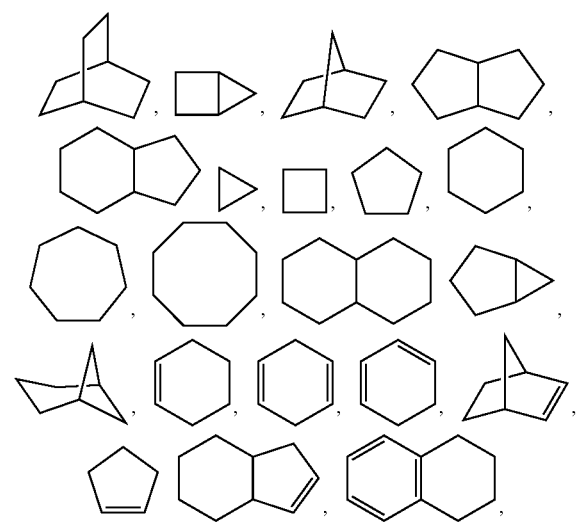

and the like. Depending on the structure, an cycloalkyl group can be a monoradical or a diradical (e.g., an cycloalkylene group).

"Cycloalkylalkyl" means an alkyl radical, as defined herein, substituted with a cycloalkyl group. Non-limiting cycloalkylalkyl groups include cyclopropylmethyl, cyclobutylmethyl, cyclopentylethyl, cyclohexylmethyl, and the like.

The term "ester" refers to a chemical moiety with formula —COOR, where R is selected from among alkyl, cycloalkyl, aryl, heteroaryl (bonded through a ring carbon) and heteroalicyclic (bonded through a ring carbon). Any hydroxy, or carboxyl side chain on the compounds described herein can be esterified. The procedures and specific groups to make such esters can be found in Greene and Wuts, Protective Groups in Organic Synthesis, 3$^{rd}$ Ed., John Wiley & Sons, New York, N.Y., 1999, which is incorporated herein by reference in its entirety.

The term "halo" or, alternatively, "halogen" or "halide" means fluoro, chloro, bromo or iodo.

The terms "haloalkyl," "haloalkenyl," "haloalkynyl" and "haloalkoxy" include alkyl, alkenyl, alkynyl and alkoxy structures in which at least one hydrogen is replaced with a halogen atom. In certain embodiments in which two or more hydrogen atoms are replaced with halogen atoms, the halogen atoms are all the same as one another. In other embodiments in which two or more hydrogen atoms are replaced with halogen atoms, the halogen atoms are not all the same as one another. The terms "fluoroalkyl" and "fluoroalkoxy" include haloalkyl and haloalkoxy groups, respectively, in which the halo is fluorine. In certain embodiments, haloalkyls are optionally substituted.

As used herein, the terms "heteroalkyl" "heteroalkenyl" and "heteroalkynyl" include optionally substituted alkyl, alkenyl and alkynyl radicals in which one or more skeletal chain atoms are selected from an atom other than carbon, e.g., oxygen, nitrogen, sulfur, silicon, phosphorus or combinations thereof.

The term "heteroatom" refers to an atom other than carbon or hydrogen. Heteroatoms are typically independently selected from among oxygen, sulfur, nitrogen, silicon and phosphorus, but are not limited to these atoms. In embodiments in which two or more heteroatoms are present, the two or more heteroatoms can all be the same as one another, or some or all of the two or more heteroatoms can each be different from the others.

As used herein, the term "ring" refers to any covalently closed structure. Rings include, for example, carbocycles (e.g., aryls and cycloalkyls), heterocycles (e.g., heteroaryls and non-aromatic heterocycles), aromatics (e.g. aryls and heteroaryls), and non-aromatics (e.g., cycloalkyls and non-aromatic heterocycles). Rings can be optionally substituted. Rings can be monocyclic or polycyclic.

As used herein, the term "ring system" refers to one, or more than one ring.

As used herein, the term "non-aromatic heterocycle", "heterocycloalkyl" or "heteroalicyclic" refers to a non-aromatic ring wherein one or more atoms forming the ring is a heteroatom. A "non-aromatic heterocycle" or "heterocycloalkyl" group refers to a cycloalkyl group that includes at least one heteroatom selected from nitrogen, oxygen and sulfur. The radicals may be fused with an aryl or heteroaryl. Heterocycloalkyl rings can be formed by three, four, five, six, seven, eight, nine, or more than nine atoms. Heterocycloalkyl rings can be optionally substituted. In certain embodiments, non-aromatic heterocycles contain one or more carbonyl or thiocarbonyl groups such as, for example, oxo- and thio-containing groups. Examples of heterocycloalkyls include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazolidine, pyrazoline, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane. Illustrative examples of heterocycloalkyl groups, also referred to as non-aromatic heterocycles, include:

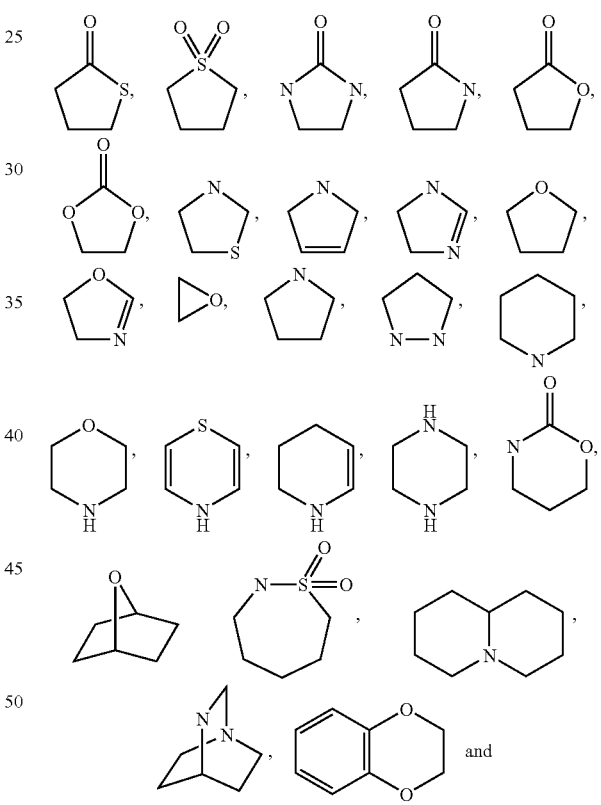

the like. The term heteroalicyclic also includes all ring forms of the carbohydrates, including but not limited to the monosaccharides, the disaccharides and the oligosaccharides. Depending on the structure, a heterocycloalkyl group can be a monoradical or a diradical (i.e., a heterocycloalkylene group).

"Heterocycloalkylalkyl" refers to an alkyl group, as defined herein, substituted with a heterocycloalkyl, as defined herein.

The term "heterocycle" refers to heteroaromatic and heteroalicyclic groups containing one to four heteroatoms each selected from O, S and N, wherein each heterocyclic group has from 4 to 10 atoms in its ring system, and with the proviso that the ring of said group does not contain two adjacent O or S atoms. Herein, whenever the number of carbon atoms in a heterocycle is indicated (e.g., $C_1$-$C_6$ heterocycle), at least one other atom (the heteroatom) must be present in the ring. Designations such as "$C_1$-$C_6$ heterocycle" refer only to the number of carbon atoms in the ring and do not refer to the total number of atoms in the ring. It is understood that the heterocylic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. Binding to a heterocycle can be at a heteroatom or via a carbon atom. Non-aromatic heterocyclic groups include groups having only 4 atoms in their ring system, but aromatic heterocyclic groups must have at least 5 atoms in their ring system. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group). Phosphorous-containing rings include, but are not limited to, 1-oxo-phospholanyl, 1-methyl-1-oxo-phosphinan-4-yl, 1-phenyl-1-oxo-phosphinan-4-yl, 1-(cyclopropylmethyl)-1-oxo-phosphinan-4-yl, 4-methyl-4-oxo-[1,4]azaphosphinan-1-yl, 4-phenyl-4-oxo-[1,4]azaphosphinan-1-yl, and 4-(cyclopropylmethyl)-4-oxo-[1,4]azaphosphinan-1-yl.

The term "membered ring" can embrace any cyclic structure. The term "membered" is meant to denote the number of skeletal atoms that constitute the ring. Thus, for example, cyclohexyl, pyridine, pyran and thiopyran are 6-membered rings and cyclopentyl, pyrrole, furan, and thiophene are 5-membered rings.

The term "moiety" refers to a specific segment or functional group of a molecule. Chemical moieties are often recognized chemical entities embedded in or appended to a molecule.

As used herein, the term "O-carboxy" or "acyloxy" refers to a group of formula RC(=O)O—.

"Alkylcarbonyloxy" refers to a (alkyl)-C(=O)O— group.

As used herein, the term "alkoxycarbonyl" refers to a group of formula —C(=O)OR.

"Carboxy" means a —C(O)OH radical.

As used herein, the term "acetyl" refers to a group of formula —C(=O)CH$_3$.

"Acyl" refers to the group —C(O)R.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, carbonyl, isocyanato, thiocyanato, isothiocyanato, nitro, perhaloalkyl, fluoroalkyl, silyl, and amino, including mono- and di-substituted amino groups, and the protected derivatives thereof. By way of example an optional substituents may be $L_sR_s$, wherein each $L_s$ is independently selected from a bond, —O—, —C(=O)—, —S—, —S(=O)—, —S(=O)$_2$—, —NH—, —NHC(O)—, —C(O)NH—, S(=O)$_2$NH—, —NHS(=O)$_2$, —OC(O)NH—, —NHC(O)O—, -(substituted or unsubstituted $C_1$-$C_6$ alkyl), or -(substituted or unsubstituted $C_2$-$C_6$ alkenyl); and each $R_1$ is independently selected from H, (substituted or unsubstituted $C_1$-$C_4$ alkyl), (substituted or unsubstituted $C_3$-$C_6$ cycloalkyl), heteroaryl, or heteroalkyl.

The compounds presented herein may possess one or more stereocenters and each center may exist in the R or S configuration. The compounds presented herein include all diastereomeric, enantiomeric, and epimeric forms as well as the appropriate mixtures thereof. Stereoisomers, if desired, may be obtained, for example, by the separation of stereoisomers by chiral chromatographic columns.

The methods and formulations described herein include the use of N-oxides, crystalline forms (also known as polymorphs), or pharmaceutically acceptable salts of compounds described herein, as well as active metabolites of these compounds having the same type of activity. In some situations, compounds may exist as tautomers. All tautomers are included within the scope of the compounds presented herein. In addition, the compounds described herein can exist in unsolvated as well as solvated forms with pharmaceutically acceptable solvents such as water, ethanol, and the like. The solvated forms of the compounds presented herein are also considered to be disclosed herein.

Neuroprotective Compounds

The neuroprotective compounds for use in the pharmaceutical compositions and methods described herein are compounds of Formula I, Formula II, and/or compounds found in Tables 2 and 3.

Neuroprotective compounds suitable for the methods described herein also can come from a variety of sources including both natural (e.g., plant extracts) and synthetic. For example, neuroprotective compounds falling within the class of triterpenes can be extracted from plants of the order Rutales, e.g., from extracts of seeds, oils, kernels, leaves and bark of various plants from the Meliaceae family, including Neem and Mahogany. See, e.g., Roy et al. (2006), *Biol Pharm Bull,* 29(2):191-201.

The neuroprotective compounds described herein are identified or characterized in an in vitro cellular assay, e.g., an assay that determines the viability of neurons or glia in the presence of a cytotoxic challenge and one or more concentrations of a candidate neuroprotective compound. Such assays are useful for identifying and testing the in vitro neuroprotective potency of candidate neuroprotective compounds.

For example, a cell viability assay can be used in a preliminary screen on a large series of compounds each of which is tested at a fixed concentration. In some embodiments, mixed hippocampal cell cultures are prepared as described in, e.g., Haughey et al. (1999), *J Neurochem,* 73(4):1363-1374, and Haughey et al (2004), *J Neurosci,* 24(1):257-268. Subsequently, the cultures are pretreated for one hour in the presence of a candidate neuroprotective agent and then incubated with a cytotoxic agent for about 18 hours. Examples of cytotoxic agents include, but are not limited to, oxidative stressors (e.g., 3-nitropropionic acid (3-NP) or $H_2O_2$), excitatory amino acids (e.g., kainate), or neurotoxic proteins (e.g., Hiv Tat, or Aβ peptides). If the survival of cell cultures in the presence of the candidate compound and the cytotoxic agent (e.g., 3-NP) is significantly greater than that of cultures incubated with the cytotoxic agent alone, the candidate test compound is considered to have neuroprotective activity. The level of protection ("percent protection") provided by the test compound at a given test concentration in vitro can be expressed as:

$$\frac{\left[\left(\begin{array}{c}\text{Cell Viability with } \textit{Cytoxic} \text{ agent} + \\ \text{Test Compound}\end{array}\right) - \right]\times 100}{\left[\begin{array}{c}\text{(Control Cell Viability (medium alone)} - \\ \text{(Cell Viability with Cytotoxic agent alone)}\end{array}\right]}$$

In some embodiments, at a concentration of 10 μM, a neuroprotective compound described herein, provides at least 6% protection against a cytotoxic agent, i.e., at least 7%, 15%, 18%, 19%, 20%, 23%, 26%, 28%, 32%, 33%, 36%, 38%, 39%, 42%, 50%, 54%, 56%, 58%, 61%, 65%, 69%, 70%, 77%, 82%, 84%, 97%, or any other percent from at least 6% to 100% protection against the cytotoxic agent.

In some embodiments, at a concentration of 10 μM, a neuroprotective compound described herein, provides greater than 100% protection, which signifies that, in addition to blocking cytotoxic agent-induced cell death, the neuroprotective compound also inhibits spontaneous cell death in the control cell cultures (i.e., cultures exposed to medium alone). In some embodiments, a neuroprotective compound described herein provides, e.g., 101, 128%, 129, or 151% protection.

A variety of methods for determining cell viability may be used. In some embodiments, cell viability is assessed based on the "MTT" assay method described in Mosmann (1983), *J Immunol Methods,* 65(1-2):55-63, or a variant thereof. This assay is based on the ability of a mitochondrial dehydrogenase enzyme from viable cells to cleave the tetrazolium rings of the pale yellow MTT and form dark blue formazan crystals, which are trapped in cells and readily quantified by ELISA spectrophotometry.

High throughput cell viability assays may be used, and are particularly useful for screening, with routine effort, a great number of candidate neuroprotective compounds or structural variants of identified neuroprotective compounds, e.g., structural variants of Formula I or Formula II described herein. See, e.g., *J Biomol Screen,* 9(6):506-515; Carrier et al. (2006), *J Neurosci Methods,* 154(1-2):239-244; See, e.g., In addition, high throughput screening systems are commercially available (see, e.g., Zymark Corp., Hoplinton, Mass.; Air Technical Industries, Mentor, Ohio; Beckman Instruments, Inc. Fullerton, Calif.; Precision Systems, Inc., Natick, Mass., etc.). These systems typically automate entire procedures including all sample and reagent pipetting, liquid dispensing, timed incubations, and final readings of the microplate in detector(s) appropriate for the assay. Automated systems thereby allow the identification and characterization of a large number of neuroprotective compounds of Formula I or Formula II without undue effort.

The neuroprotective compounds described herein, e.g., those of Formula I or Formula II, can be used for the manufacture of a medicament for treating any of the foregoing neurodegenerative conditions (e.g., multiple sclerosis, Alzheimer's disease, stroke, or spinal cord injury).

In some embodiments, a neuroprotective compound used for the methods described herein in vitro $ED_{50}$ for neuroprotection of less than 100 μM (e.g., less than 10 μM, less than 5 μM, less than 4 μM, less than 3 μM, less than 1 μM, less than 0.8 μM, less than 0.6 μM, less than 0.5 μM, less than 0.4 μM, less than 0.3 μM, less than less than 0.2 μM, less than 0.1 μM, less than 0.08 μM, less than 0.06 μM, less than 0.05 μM, less than 0.04 μM, less than 0.03 μM, less than less than 0.02 μM, less than 0.01 HIM, less than 0.0099 μM, less than 0.0098 μM, less than 0.0097 μM, less than 0.0096 μM, less than 0.0095 μM, less than 0.0094 μM, less than 0.0093 μM, less than 0.00092, or less than 0.0090 μM).

Examples of Pharmaceutical Compositions and Methods of Administration

The pharmaceutical solid dosage forms described herein can include a compound of Formula I or Formula II, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound of Formula I or Formula II. In one embodiment, some or all of the particles of the compound of Formula I or Formula II are coated. In another embodiment, some or all of the particles of the compound of Formula I or Formula II are microencapsulated. In still another embodiment, the particles of the compound of Formula I or Formula II are not microencapsulated and are uncoated.

Pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., "The Theory and Practice of Industrial Pharmacy" (1986). Other methods include, e.g., spray drying, pan coating, melt granulation, granulation, fluidized bed spray drying or coating (e.g., wurster coating), tangential coating, top spraying, tableting, extruding and the like.

Provided herein are pharmaceutical compositions that include one or more neuroprotective compounds described herein and a pharmaceutically acceptable diluent(s), excipient(s), or carrier(s). In addition, the compounds described herein can be administered as pharmaceutical compositions in which compounds described herein are mixed with other active ingredients, as in combination therapy. In some embodiments, the pharmaceutical compositions may include other medicinal or pharmaceutical agents, carriers, adjuvants, such as preserving, stabilizing, wetting or emulsifying agents, solution promoters, salts for regulating the osmotic pressure, and/or buffers. In addition, the pharmaceutical compositions can also contain other therapeutically valuable substances.

In certain embodiments, compositions may also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

A pharmaceutical composition, as used herein, refers to a mixture of a compound described herein, such as, for example, compounds of Formula I or Formula II with other chemical components, such as carriers, stabilizers, diluents, dispersing agents, suspending agents, thickening agents, and/or excipients. The pharmaceutical composition facilitates administration of the compound to an organism. In practicing the methods of treatment or use provided herein, therapeutically effective amounts of compounds described herein are administered in a pharmaceutical composition to a mammal having a neurodegenerative condition, disease, or disorder to be treated. Preferably, the mammal is a human. A therapeutically effective amount can vary widely depending on the severity and stage of the condition, the age and relative health of the subject, the potency of the compound used and other factors. The compounds can be used singly or in combination with one or more therapeutic agents as components of mixtures.

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound described herein may be manufactured, by way of example only, by means of mixing, dissolving, granulating, dragee-making, levigating, emulsifying, encapsulating, entrapping or compression processes.

The pharmaceutical compositions will include at least one compound described herein, such as, for example, a compound of Formula I or Formula II, as an active ingredient in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. In some situations, compounds may exist as tautomers. All tautomers are included within the scope of the compounds presented herein. Additionally, the compounds described herein can exist in unsolvated as well as solvated forms with pharmaceutically acceptable solvents such as water, ethanol, and the like. The solvated forms of the compounds presented herein are also considered to be disclosed herein.

"Antioxidants" include, for example, butylated hydroxytoluene (BHT), sodium ascorbate, ascorbic acid, sodium metabisulfite and tocopherol. In certain embodiments, antioxidants enhance chemical stability where required.

In certain embodiments, compositions provided herein may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

Formulations described herein may benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

"Bioavailability" refers to the percentage of the weight of compounds disclosed herein, such as, compounds of Formula I or Formula II, that is delivered into the general circulation of the animal or human being studied. The total exposure (AUC (0-∞)) of a drug when administered intravenously is usually defined as 100% bioavailable (F %). "Oral bioavailability" refers to the extent to which compounds disclosed herein, such as, compounds of Formula I or Formula II that are absorbed into the general circulation when the pharmaceutical composition is taken orally as compared to intravenous injection.

"Blood plasma concentration" refers to the concentration of compounds disclosed herein, such as, compounds of Formula I or Formula II, in the plasma component of blood of a subject. It is understood that the plasma concentration of compounds of Formula I or Formula II may vary significantly between subjects, due to variability with respect to metabolism and/or possible interactions with other therapeutic agents. In accordance with one embodiment disclosed herein, the blood plasma concentration of the compounds of Formula I or Formula II may vary from subject to subject. Likewise, values such as maximum plasma concentration (Cmax) or time to reach maximum plasma concentration (Tmax), or total area under the plasma concentration time curve (AUC (0-∞)) may vary from subject to subject Due to this variability, the amount necessary to constitute "a therapeutically effective amount" of a compound of Formula I or Formula II may vary from subject to subject.

"Carrier materials" include any commonly used excipients in pharmaceutics and should be selected on the basis of compatibility with compounds disclosed herein, such as, compounds of Formula I or Formula II, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may include, but are not limited to, acacia, gelatin, colloidal silicon dioxide, calcium glycerophosphate, calcium lactate, maltodextnin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol CPVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The term "disintegrate" includes both the dissolution and dispersion of the dosage form when contacted with gastrointestinal fluid. "Disintegration agents or disintegrants" facilitate the breakup or disintegration of a substance. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

"Drug absorption" or "absorption" typically refers to the process of movement of drug from site of administration of a drug across a barrier into a blood vessel or the site of action, e.g., a drug moving from the gastrointestinal tract into the portal vein or lymphatic system.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. An appropriate "effective" amount in any individual case may be determined using techniques, such as a dose escalation study.

An "enteric coating" is a substance that remains substantially intact in the stomach but dissolves and releases the drug in the small intestine or colon. Generally, the enteric coating comprises a polymeric material that prevents release in the low pH environment of the stomach but that ionizes at a higher pH, typically a pH of 6 to 7, and thus dissolves sufficiently in the small intestine or colon to release the active agent therein.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Flavoring agents" and/or "sweeteners" useful in the formulations described herein, include, e.g., acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sylitol, sucralose, sorbitol, Swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanllla-mint, and mixtures thereof.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Sterowet®, boric acid, sodium benzoate, sodium acetate, sodium chloride, leucine, a polyethylene glycol (e.g., PEG4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

A "measurable serum concentration" or "measurable plasma concentration" describes the blood serum or blood plasma concentration, typically measured in mg, μg, or ng of therapeutic agent per ml, dl, or l of blood serum, absorbed into the bloodstream after administration. As used herein, measurable plasma concentrations are typically measured in ng/ml or μg/ml.

The terms "neuroprotective," "neuroprotection," or "neuroprotectant," as used herein refer to the ability of an agent (e.g., a compound described herein) to significantly prevent or reduce the occurrence of spontaneous or induced death (e.g., by apoptosis) of neurons or glia in vitro or in vivo, relative to the ability of a control reagent (e.g., cell culture medium, or a drug vehicle such as DMSO).

A "prognostic biomarker," as referred to herein, is any molecular, biochemical, metabolic, cellular, or structural entity (or a ratio of such entities), the presence or level of which relates to a likelihood of developing, suffering from, or having a relapse of a pathological condition.

"Pharmacodynamics" refers to the factors which determine the biologic response observed relative to the concentration of drug at a site of action.

"Pharmacolinetics" refers to the factors which determine the attainment and maintenance of the appropriate concentration of drug at a site of action.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

The term "prophylactically effective amount," as used herein, refers that amount of a composition applied to a patient which will relieve to some extent one or more of the symptoms of a disease, condition or disorder being treated. In such prophylactic applications, such amounts may depend on the patient's state of health, weight, and the like.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Steady state," as used herein, is when the amount of drug administered is equal to the amount of drug eliminated within one dosing interval resulting in a plateau or constant plasma drug exposure.

The term "subject" as used herein, refers to an animal which is the object of treatment, observation or experiment By way of example only, a subject may be, but is not limited to, a mammal including, but not limited to, a human.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants may be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium docusate, triacetin, Tween 80, vitamin E TPGS, ammonium salts and the like.

The compositions described herein can be formulated for administration to a subject via any means including, but not limited to, oral, parenteral (e.g., intravenous, subcutaneous, or intramuscular), buccal, intranasal, rectal or transdermal administration routes. As used herein, the term "subject" is used to mean an animal, preferably a mammal, including a human or non-human. The terms patient and subject may be used interchangeably.

Moreover, the pharmaceutical compositions described herein, which include a compound of Formula I or Formula II, can be formulated into any suitable dosage form, including but not limited to, aqueous oral dispersions, liquids, gels, syrups, elixirs, slurries, suspensions and the like, for oral ingestion by a patient to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacinth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound of Formula I or Formula II, with one or more pharmaceutical excipients to form a bulk blend composition. When referring to these bulk blend compositions as homogeneous, it is meant that the particles of the compound of Formula I or Formula II, are dispersed evenly throughout the composition so that the composition may be readily subdivided into equally effective unit dosage forms, such as tablets, pills, and capsules. The individual unit dosages may also include film coatings, which disintegrate upon oral ingestion or upon contact with diluent. These formulations can be manufactured by pharmacological techniques.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds of Formula I or Formula II, which sufficiently isolate the compound of Formula I or Formula II from other non-compatible excipients. Materials compatible with compounds of Formula I or Formula II are those that delay the release of the compounds of Formula I or Formula II in vivo.

Exemplary microencapsulation materials useful for delaying the release of the formulations including compounds of Formula I or Formula II, include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®&, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit®& L30D-55, Eudragit® FS 30D Eudragit® L100-55, Eudragit®& L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

In still other embodiments, plasticizers such as polyethylene glycols, e.g., PEG 300, PEG 400, PEG 600, PEG 1450, PEG 3350, and PEG 800, stearic acid, propylene glycol, oleic acid, and triacetin are incorporated into the microencapsulation material. In other embodiments, the microencapsulating material useful for delaying the release of the pharmaceutical compositions is from the USP or the National Formulary (NF). In yet other embodiments, the microencapsulation material is Klucel. In still other embodiments, the microencapsulation material is methocel. Microencapsulated compounds of Formula I or Formula II may be formulated. Such methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

In one embodiment, the particles of compounds of Formula I or Formula II are microencapsulated prior to being formulated into one of the above forms. In still another embodiment, some or most of the particles are coated prior to being further formulated by using standard coating procedures, such as those described in Remington's Pharmaceutical Sciences, 20th Edition (2000).

In other embodiments, the solid dosage formulations of the compounds of Formula I or Formula II are plasticized (coated) with one or more layers. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

The pharmaceutical solid oral dosage forms including formulations described herein, which include a compound of Formula I or Formula II, can be further formulated to provide a controlled release of the compound of Formula I or Formula II. Controlled release refers to the release of the compound of Formula I or Formula II from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein can be formulated as enteric coated delayed release oral dosage forms, i.e., as an oral dosage form of a pharmaceutical composition as described herein which utilizes an enteric coating to affect release in the small intestine of the gastrointestinal tract. The enteric coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated.

The term "delayed release" as used herein refers to the delivery so that the release can be accomplished at some generally predictable location in the intestinal tract more distal to that which would have been accomplished if there had been no delayed release alterations. In some embodiments the method for delay of release is coating. Any coatings should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. In some embodiments the polymers for use in the present invention are anionic carboxylic polymers.

In other embodiments, the formulations described herein, which include a compound of Formula I or Formula II, are delivered using a pulsatile dosage form. A pulsatile dosage form is capable of providing one or more immediate release pulses at predetermined time points after a controlled lag time or at specific sites. Pulsatile dosage forms including the formulations described herein, which include a compound of Formula I or Formula II, may be administered using a variety of pulsatile formulations. For example, such formulations include, but are not limited to, those described in U.S. Pat. Nos. 5,011,692, 5,017,381, 5,229,135, and 5,840,329. Other pulsatile release dosage forms suitable for use with the present formulations include, but are not limited to, for example, U.S. Pat. Nos. 4,871,549, 5,260,068, 5,260,069, 5,508,040, 5,567,441 and 5,837,284. In one embodiment, the controlled release dosage form is pulsatile release solid oral dosage form including at least two groups of particles, (i.e. multiparticulate) each containing the formulation described herein. The first group of particles provides a substantially immediate dose of the compound of Formula I or Formula II upon ingestion by a mammal. The first group of particles can be either uncoated or include a coating and/or sealant. The second group of particles includes coated particles, which includes from about 2% to about 75%, preferably from about 2.5% to about 70%, and more preferably from about 40% to about 70%, by weight of the total dose of the compound of Formula I or Formula II in said formulation, in admixture with one or more binders. The coating includes a pharmaceutically acceptable ingredient in an amount sufficient to provide a delay of from about 2 hours to about 7 hours following ingestion before release of the second dose. Suitable coatings include one or more differentially degradable coatings such as, by way of example only, pH sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40D®) either alone or blended with cellulose derivatives, e.g., ethylcellulose, or non-enteric coatings having variable thickness to provide differential release of the formulation that includes a compound of Formula I or Formula II.

Additional examples of controlled release delivery systems include, e.g., polymer-based systems, such as polylactic and polyglycolic acid, plyanhydrides and polycaprolactone; porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using binders and the like. See, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to the particles of compound of Formula I or Formula II, the liquid dosage forms may include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions can further include a crystalline inhibitor.

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropyl cellulose ethers (e.g., HPC, HPC-SL, and HPC-L), hydroxypropyl methylcellulose and hydroxypropyl methylcellulose ethers (e.g. HPMC K100, HPMC K4M, HPMC K15M, and HPMC K100M), carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents suitable for the aqueous suspensions and dispersions include, but are not limited to, cetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carbopol 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof. In one embodiment, the aqueous liquid dispersion can comprise a sweetening agent or flavoring agent in a concentration ranging from about 0.001% to about 1.0% the volume of the aqueous dispersion. In another embodiment, the aqueous liquid dispersion can comprise a sweetening agent or flavoring agent in a concentration ranging from about 0.005% to about 0.5% the volume of the aqueous dispersion. In yet another embodiment, the aqueous liquid dispersion can comprise a sweetening agent or flavoring agent in a concentration ranging from about 0.01% to about 1.0% the volume of the aqueous dispersion.

In addition to the additives listed above, the liquid formulations can also include inert diluents such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

It is to be appreciated that there is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Intranasal formulations of a compound of Formula I or Formula II can be prepared by adapting the methods described in U.S. Pat. Nos. 4,476,116, 5,116,817 and 6,391,452. Formulations that include a compound of Formula I or Formula II, which are prepared according to these and other techniques are prepared as solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients can be found in REMINGTON: THE SCIENCE-AND PRACTICE OF PHARMACY, 21st edition, 2005, a standard reference in the field. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds of Formula I or Formula II described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds of Formula I or Formula II may be administered using a variety of formulations. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound of Formula I or Formula II, is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, it will be appreciated that virtually any such carrier can be used, so long as the desired drug release profile is not compromised, and the carrier is compatible with the compound of Formula I or Formula II, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels.

Transdermal formulations described herein may be administered using a variety of devices that include, but are not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients. In one embodiments, the transdermal formulations described herein include at least three components: (1) a formulation of a compound of Formula I or Formula II; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds of Formula I or Formula II. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations that include a compound of Formula I or Formula II, suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations may include aqueous or nonaqueous solutions, preferably with physiologically compatible buffers or excipients.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein can also include an mucoadhesive polymer, selected from among, for example, carboxymethylcellulose, carbomer (acrylic acid polymer), poly(methylmethacrylate), polyacrylamide, polycarbophil, acrylic acid/butyl acrylate copolymer, sodium alginate and dextran.

In some embodiments, the compounds described herein may be administered topically and can be formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

In other embodiments, the formulations described herein, which include a compound of Formula I or Formula II, are blood brain barrier-permeable (BBB-permeable) nanoparticle formulations. Methods of producing such BBB-permeable nanoparticle formulations include, but are not limited to, for example, U.S. Pat. Nos. 6,117,454 and 7,025,991.

Examples of Methods of Dosing and Treatment Regimens

The compounds described herein can be used in the preparation of medicaments for the treatment of neurodegenerative diseases or conditions that would benefit, at least in part, from neuroprotection. In addition, a method for treating any of the diseases or conditions described herein in a subject in need of such treatment, involves administration of pharmaceutical compositions containing at least one compound of Formula I or Formula II described herein, or a pharmaceutically acceptable salt, pharmaceutically acceptable N-oxide, pharmaceutically active metabolite, pharmaceutically acceptable prodrug, or pharmaceutically acceptable solvate thereof, in therapeutically effective amounts to said subject.

The compositions containing the compound(s) described herein can be administered for prophylactic and/or therapeutic treatments. In therapeutic applications, the compositions are administered to a patient already suffering from a disease or condition, in an amount sufficient to cure or at least partially arrest the symptoms of the disease or condition. Amounts effective for this use will depend on the severity and course of the disease or condition, previous therapy, the patient's health status, weight, and response to the drugs, and the judgment of the treating physician.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease or condition and its severity, the identity (e.g., weight) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment will typically be in the range of 0.02-5000 mg per day, preferably 1-1500 mg per day. The desired dose may conveniently be presented in a single dose or as divided doses administered simultaneously (or over a short period of time) or at appropriate intervals, for example as two, three, four or more sub-doses per day.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

The daily dosages appropriate for the compounds described herein described herein are from about 0.01 to 2.5 mg/kg per body weight. An indicated daily dosage in the larger mammal, including, but not limited to, humans, is in the range from about 0.5 mg to about 100 mg, conveniently administered in divided doses, including, but not limited to, up to four times a day or in extended release form. Suitable unit dosage forms for oral administration include from about 1 to 50 mg active ingredient. The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it can be expressed as the ratio between LD50 and ED50. Compounds exhibiting high therapeutic indices are preferred. The data obtained from cell culture assays and animal studies can be used in formulating a range of dosage for use in human. The dosage of such compounds lies preferably within a range of circulating concentrations that include the ED50 with minimal toxicity. The dosage may vary within this range depending upon the dosage form employed and the route of administration utilized.

Combination Treatments

The neuroprotective compound compositions described herein can also be used in combination with other therapeutic reagents that are selected for their therapeutic value for the condition to be treated. In general, the compositions described herein and, in embodiments where combinational therapy is employed, other agents do not have to be administered in the same pharmaceutical composition, and may, because of different physical and chemical characteristics, have to be administered by different routes.

In certain instances, it may be appropriate to administer at least one neuroprotective compound described herein in combination with another therapeutic agent. By way of example only, if one of the side effects experienced by a patient upon receiving one of the neuroprotective compounds described herein is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with one or more (e.g., one, two, or three) other therapeutic agents (which also includes a therapeutic regimen) that also have a therapeutic benefit. In any case, regardless of the disease, disorder or condition being treated, the overall benefit experienced by the patient may simply be additive of the multiple therapeutic agents or the patient may experience a synergistic (i.e., a greater than additive) benefit due to their specific combination.

The compounds may be administered concurrently (e.g., simultaneously, essentially simultaneously or within the same treatment protocol) or sequentially, depending upon the nature of the disease, disorder, or condition, the condition of the patient, and the actual choice of compounds used.

In any case, the multiple therapeutic agents (one of which is a compound of Formula I or Formula II described herein) may be administered in any order, or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations is also envisioned.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease or condition, and the timing of administering the composition containing a compound can vary. Thus, for example, the compounds can be used as a prophylactic and can be administered continuously to subjects with a propensity to develop conditions or diseases in order to prevent the occurrence of the disease or condition. A compound is preferably administered as soon as is practicable after the onset of a disease or condition is detected or suspected, and for a length of time necessary for the treatment of the disease, such as, for example, from about 1 month to about 3 months. The length of treatment can vary for each subject. For example, the compound or a formulation containing the compound can be administered for at least 2 weeks, about 1 month to about 5 years, and from about 1 month to about 3 years.

Exemplary Therapeutic Agents for Use in Combination with a Neuroprotective Compound Agents for Treating Multiple Sclerosis Where a subject is suffering from or at risk of suffering from multiple sclerosis, a neuroprotective compound disclosed herein can be used together with one or more of the following exemplary multiple sclerosis therapeutic agents in any combination: Interferon β-1a, Interferon β-1b, glatiramer acetate (Copaxone®), mitoxantrone (Novantrone®), low dose naltrexone, Natalizumab (Tysabri®), Sativex®, Aimspro (Goats Serum), Trimesta (Oral Estriol), Laquinimod, FTY720 (Fingolimod), MBP8298, NeuroVax™, Tovaxin™, Revimmune, CHR-1103, BHT-3009, BG-12, Cladribine, daclizumab (Zenapax) Rituximab (Rituxan), cyclophosphamide, Campath, Fampridine-SR, MN-166, Temsirolimus, or RPI-78M.

Agents for Treating Dementia (e.g. Alzheimer's Disease or AIDS-Related Dementia)

Where a subject is suffering from or at risk of suffering from dementia, a neuroprotective compound disclosed herein can be used together with one or more agents or methods for treating dementia in any combination. Examples of therapeutic agents/treatments for treating dementia include, but are not limited to any of the following Flurizan™ (MPC-7869, r flurbiprofen), memantine, galantamine, rivastigmine, donezipil, tacrine, $A\beta_{1-42}$ immunotherapy, resveratrol, (−)-epigallocatechin-3-gallate, statin, vitamin C, or vitamin E.

Agents for Treating Parkinson's Disease

Where a subject is suffering from or at risk of suffering from Parkinson's Disease, a neuroprotective compound disclosed herein can be used together with one or more agents or methods for treating Parkinson's disease in any combination. Examples of therapeutic agents/treatments for treating Parkinson's Disease include, but are not limited to any of the following: L-dopa, carbidopa, benserazide, tolcapone, entacapone, bromocriptine, pergolide, pramipexole, ropinirole, cabergoline, apomorphine, lisuride, selegiline, or rasagiline.

Agents for Treating Amyotrophic Lateral Sclerosis

Where a subject is suffering from or at risk of suffering from Amyotrophic Lateral Sclerosis, a neuroprotective compound disclosed herein can be used together with one or more agents or methods for treating Amyotrophic Lateral Sclerosis in any combination. Examples of therapeutic agents/treatments for treating Parkinson's Disease include, but are not limited to any of the following: riluzole, insulin-like growth factor 1, or ketogenic diet.

Agents for Treating Huntington's Disease

Where a subject is suffering from or at risk of suffering from Huntington's Disease, a neuroprotective compound disclosed herein can be used together with one or more agents or methods for treating Huntington's Disease in any combination. Examples of therapeutic agents/treatments for treating Huntington's Disease include, but are not limited to any of the following: dopamine receptor blockers, creatine, CoQ10, minocycline, exercise, antioxidants, antidepressants (notably, but not exclusively, selective serotonin reuptake inhibitors SSRIs, such as sertraline, fluoxetine, and paroxetine), dopamine antagonists, (e.g., tetrabenazine), or RNAi-mediated silencing of mutant Huntingtin expression.

Agents for Treating Autoimmune Inflammatory, or Allergic conditions

Where a subject is suffering from or at risk of suffering from an autoimmune, inflammatory disease, or allergic condition that affects the nervous system (see, e.g., Allan et al. (2003), *Philos Trans R Soc Lond B Biol Sci,* 358(1438): 1669-1677), a neuroprotective compound disclosed herein can be used together with one or more of the following therapeutic agents in any combination: immunosuppressants (e.g., tacrolimus, cyclosporin, rapamicin, methotrexate, cyclophosphamide, azathioprine, mercaptopurine, mycophenolate, or FTY720), glucocorticoids (e.g., prednisone, cortisone acetate, prednisolone, methylprednisolone, dexamethasone, betamethasone, triamcinolone, beclometasone, fludrocortisone acetate, deoxycorticosterone acetate, aldosterone), non-steroidal anti-inflammatory drugs (e.g., salicylates, arylalkanoic acids, 2-arylpropionic acids, N-arylanthranilic acids, oxicams, coxibs, or sulphonanilides), Cox-2-specific inhibitors (e.g., valdecoxib, celecoxib, or rofecoxib), leflunomide, gold thioglucose, gold thiomalate, aurofin, sulfasalazine, hydroxychloroquinine, minocycline, TNF-α binding proteins (e.g., infliximab, etanercept, or adalimumab), abatacept, anakinra, interferon-β, interferon-γ, interleukin-2, allergy vaccines, antihistamines, antileukotrienes, beta-agonists, theophylline, or anticholinergics.

Agents for Treating Thromboembolic Disorders

Where a subject is suffering from or at risk of suffering from a thromboembolic disorder (e.g., stroke), the subject can be treated with a neuroprotective compound disclosed herein in any combination with one or more other anti-thromboembolic agents. Examples of anti-thromboembolic agents include, but are not limited any of the following: thrombolytic agents (e.g., alteplase anistreplase, streptokinase, urokinase, or tissue plasminogen activator), heparin, tinzaparin, warfarin, dabigatran (e.g., dabigatran etexilate), factor Xa inhibitors (e.g., fondaparinux, draparinux, rivaroxaban, DX-9065a, otamixaban, LY517717, or YM150), ticlopidine, clopidogrel, CS-747 (prasugrel, LY640315), ximelagatran, or BIBR 1048.

Agents for Treating an HV Infection

Where the subject is suffering from an HIV infection (e.g., suffering from AIDS), any of the neuroprotective compounds disclosed herein can be administered to the subject prophylactically or therapeutically to treat AIDs-related dementia in combination with one or more anti-HIV compounds administered to treat the HIV infection. Examples of anti-HIV compounds include, but are not limited to, AZT (zidovudine, Retrovir), ddI (didanosine, Videx), 3TC (lamivudine, Epivir), d4T (stavudine, Zerit), abacavir (Ziagen), and FTC (emtricitabine, Emtriva), tenofovir (Viread), efavirenz (Sustiva), nevirapine (Viramune), lopinavir/ritonavir (Kaletra), indinavir (Crixivan), ritonavir (Norvir), nelfinavir (Viracept), saquinavir hard gel capsules (Invirase), atazanavir (Reyataz), amprenavir (Agenerase), fosamprenavir (Telzir), tipranavir (Aptivus), or T20 (enfuvirtide, Fuzeon)

Antipsychotic Compounds

Where the subject is suffering from schizophrenia, which has recently been found to be characterized by a progressive neurodegenerative process (see, e.g., Perez-Neri et al. (2006), *Neurochem Res,* 31(10):1279-1294), any of the neuroprotective compounds disclosed herein can be administered to the subject prophylactically or therapeutically in combination with one or more antipsychotic compounds for treatment of schizophrenia. Examples of antipsychotic compounds include, but are not limited to, clozapine, risperidone, olanzapine, quetiapine, ziprasidone, aripiprazole, paliperidone, sertindole, zotepine, amisulpride, bifeprunox, melperone, chlorpromazine (largactil, thorazine), fluphenazine, haloperidol, molindone, thiothixene, thioridazine, trifluoperazine, loxapine, perphenazine, prochlorperazine, pimozide, thiothixene, or zuclopenthixol.

Antiepileptic Compounds

Where the subject is suffering from epilepsy, any of the neuroprotective compounds disclosed herein can be administered to the subject prophylactically or therapeutically in combination with one or more antiepileptic compounds.

Examples of antiepileptic compounds include, but are not limited to, carbamazepine, clobazam, clonazepam, ethosuximide, felbamate, fosphenyloin, flurazepam, gabapentin, lamotrigine, levetiracetam, oxcarbazepine, mephenyloin, phenobarbital, phenyloin, pregabalin, primidone, sodium valproate, tiagabine, topiramate, valproate semisodium, valproic acid, vigabatrin, diazepam, or lorazepam.

Neuroprotective Compounds and Compositions

In some embodiments, one or more of the neuroprotective modified terpenoid compounds disclosed herein can be used in combination with one or more neuroprotective compounds or compositions to treat a subject suffering from or at risk of neurodegenerative condition. Examples of neuroprotective compounds include, but are not limited to, any of the following: resveratrol, GPI 1046, epigallocatechin gallate, α-lipoic acid, Omega-3 fatty acids (e.g., docosahexaenoic acid or eicosapentaenoic acid), Vitamin E (tocopherol), carnitine, cytidine diphosphocoline (citicholine), coenzyme Q10, curcumin, salviolonic acid B, folic acid, Gingko biloba extract, ginsenoside Rb1, ginsenoside Rg3, L-Glutathione, grape seed extract, lutein, zeaxanthin, methylcobalamin, N-acetyl-L-cysteine, pycnogenol, quercetin, or taurine.

EXAMPLES

The following specific examples are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety. Where reference is made to a URL or other such identifier or address, it is understood that such identifiers can change and particular information on the internet can come and go, but equivalent information can be found by searching the internet Reference thereto evidences the availability and public dissemination of such information.

Example 1

Identification of Neuroprotective Compounds

Figure 2:
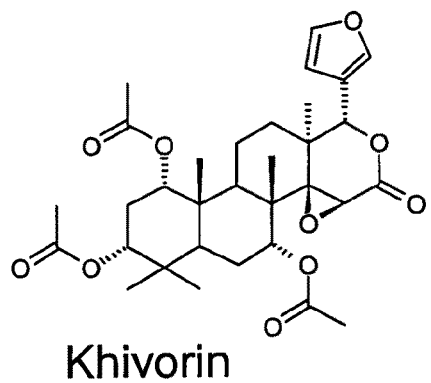
FIG. 2 shows the chemical structures of five of the neuroprotective compounds as described herein.
Figure 2:
Figure 2:
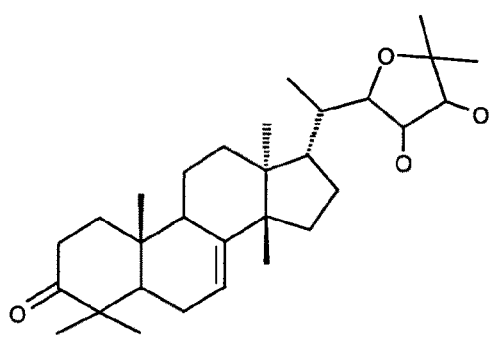
Figure 2:
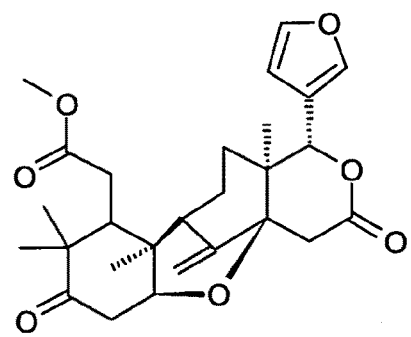
Figure 2:
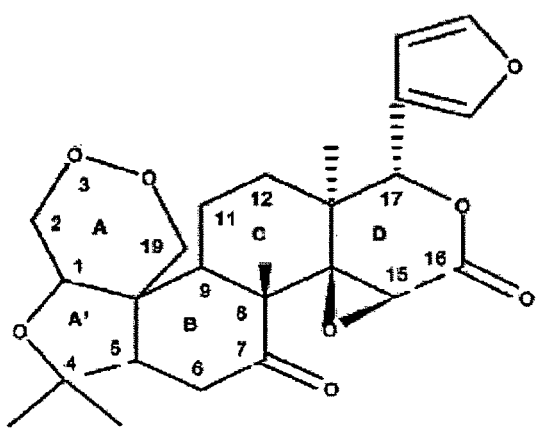

We sought to identify neuroprotective compounds using an in vitro neuroprotection assay as described in detail below. We screened a specific collection/library of compounds that we identified as potentially active agents. This particular collection contains 2000 compounds of which 50% are FDA-approved compounds, 30% are natural products, and 20% are other bioactive compounds. As shown in FIG. 1, the vast majority of the compounds conferred little or no neuroprotection or were even neurotoxic, with only about 3% exhibiting neuroprotective activity. From this subset of potential compounds (I.e., those exhibiting neuroprotective activity), we selected a further limited group of modified terpenoids. A larger series of modified terpenoid compounds was then screened in the same type of assay as described below. Exemplary neuroprotective modified terpenoids are shown in FIG. 2.

Example 2

Pharmaceutical Compositions

Example 2a

Parenteral Composition

To prepare a parenteral pharmaceutical composition suitable for administration by injection, 100 mg of a water-soluble salt of a compound of any of Formula I, Formula II, Table 2 or Table 3, is dissolved in DMSO and then mixed with 10 mL of 0.9% sterile saline. The mixture is incorporated into a dosage unit form suitable for administration by injection.

Example 2b

Oral Composition

To prepare a pharmaceutical composition for oral delivery, 100 mg of a compound of any of Formula I, Formula II, Table 2 or Table 3, is mixed with 750 mg of starch. The mixture is incorporated into an oral dosage unit for, such as a hard gelatin capsule, which is suitable for oral administration.

Example 2c

Sublingual (Hard Lozenge) Composition

To prepare a pharmaceutical composition for buccal delivery, such as a hard lozenge, mix 100 mg of a compound of any of Formula I, Formula II, Table 2 or Table 3, with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 2d

Inhalation Composition

To prepare a pharmaceutical composition for inhalation delivery, 20 mg of a compound of any of Formula I, Formula II, Table 2 or Table 3, is mixed with 50 mg of anhydrous citric acid and 100 mL of 0.9% sodium chloride solution. The mixture is incorporated into an inhalation delivery unit, such as a nebulizer, which is suitable for inhalation administration.

Example 2e

Rectal Gel Composition

To prepare a pharmaceutical composition for rectal delivery, 100 mg of a compound of any of Formula I, Formula II, Table 2 or Table 3, is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 2f

Topical Gel Composition

To prepare a pharmaceutical topical gel composition, 100 mg of a compound of any of Formula I, Formula II, Table 2 or Table 3, is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 2g

Ophthalmic Solution Composition

To prepare a pharmaceutical opthalmic solution composition, 100 mg of a compound of any of Formula I, Formula II, Table 2 or Table 3, is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration. Example 3: Biological Assays and Analyses

Example 3A

Exemplary Modified Terpenoids are Neuroprotective against an Oxidative Stressor and a Neurotoxic Protein We sought to evaluate the protective efficacy of a number of modified terpenoid compounds against the against many different neurotoxins, ranging from the chemotoxic 6-OHDA, NMDA, 3-nitropropionic acid (3-NP), and viral proteins such as Tat and gp120. Thus, we established an in vitro neuroprotection assay using rat mixed hippocampal cultures, in which we evaluated the protective efficacy of neuroprotective compounds disclosed herein. The oxidative stressor 3-NP was used to elicit toxicity in the rat hippocampal cultures to mimic the oxidative damage, reactive oxygen species production and ensuing neurodegeneration resulting from HIV infection. Another measure of neurotoxicity which results from HIV infection was evaluated by exposure of the hippocampal cultures to HIV-1 Tat (Li et al (2005), Neurotox Res, 8(1-2): 119-134).

Rat mixed hippocamal neuronal cultures were generated from freshly dissected rat hippocampi (embryonic day 18) in neurobasal media containing 5% fetal bovine serum and 2% B27 supplement. The cells were plated into 96 well plates at a density of $4 \times 10^5$ cells/mL and routinely used on days 11-14 following culturing. Cell viability was assessed with MTT [3-(4,5-dimethylthiazol-2-yl)-2,5-diphenyltetrazolium bromide] assay. The MTT assay is based on the ability of a mitochondrial dehydrogenase enzyme from viable cells to cleave the tetrazolium rings of the pale yellow MTT and form dark blue formazan crystals. See Mosmann (1983), *J Immunol Methods*, 65(1-2):55-63. These crystals are largely impermeable to cell membranes, and thus accumulate within healthy cells. The resultant formazan precipitates are solubilized with DMSO and read on a multiwell scanning spectrophotometer (ELISA reader). The number of surviving cells is directly proportional to the level of the formazan product created.

Figure 3:
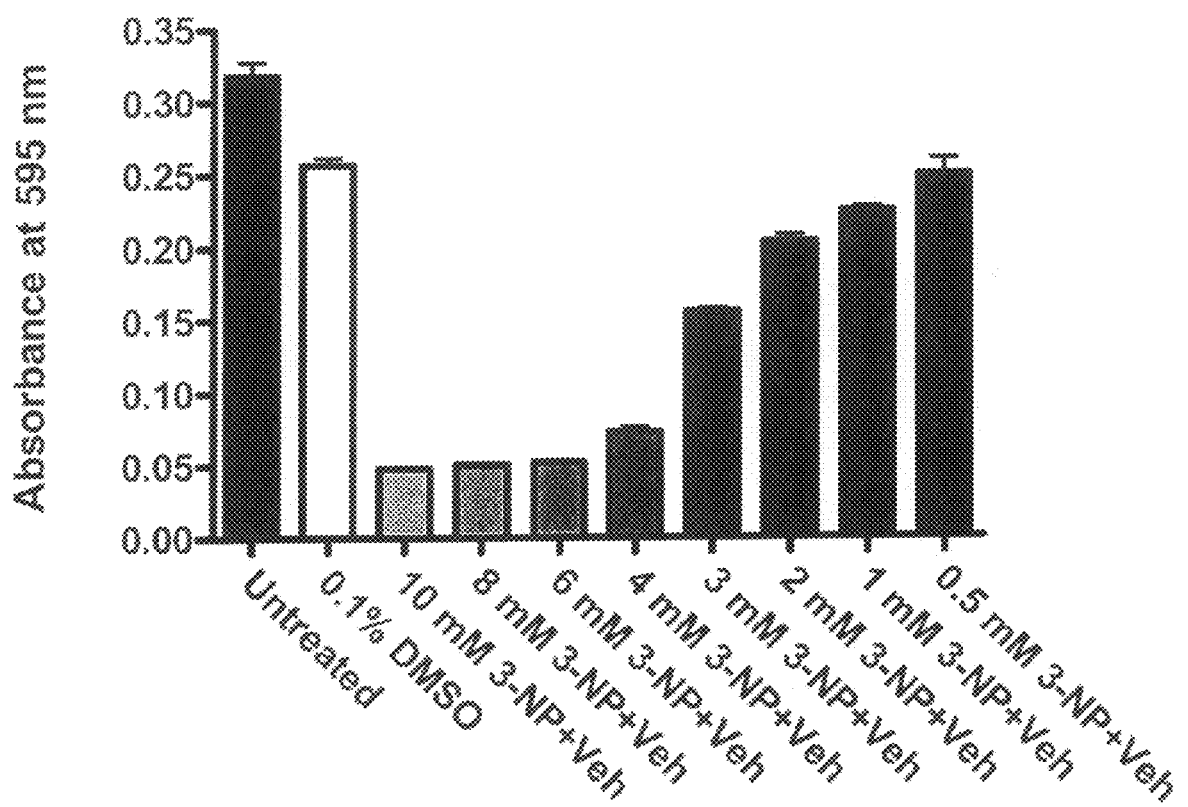
FIG. 3 is a bar graph showing the effect of a series of 3-nitropropionic acid (3-NP) concentrations (0.5-10 mM) on survival of mixed hippocampal cell cultures in a [3-(4,5-dimethylthiazol-2-yl)-2,5-diphenyl tetrazolium bromide] (MTT) viability assay. Absorbance at 595 nm (corresponding to the absorbance of the reduced MTT formazan product) is directly proportional to cell viability.

Mixed hippocampal cultures were incubated with 3-NP (0.5-10 mM) for 18 hours and then assessed for viability using an MTT assay. As shown in FIG. 3, titration of 3-NP levels for neurotoxic effects demonstrated that 3 mM 3-NP treatment consistently induced 25-35% cytotoxicity in rat mixed hippocampal cultures.

Figure 4:
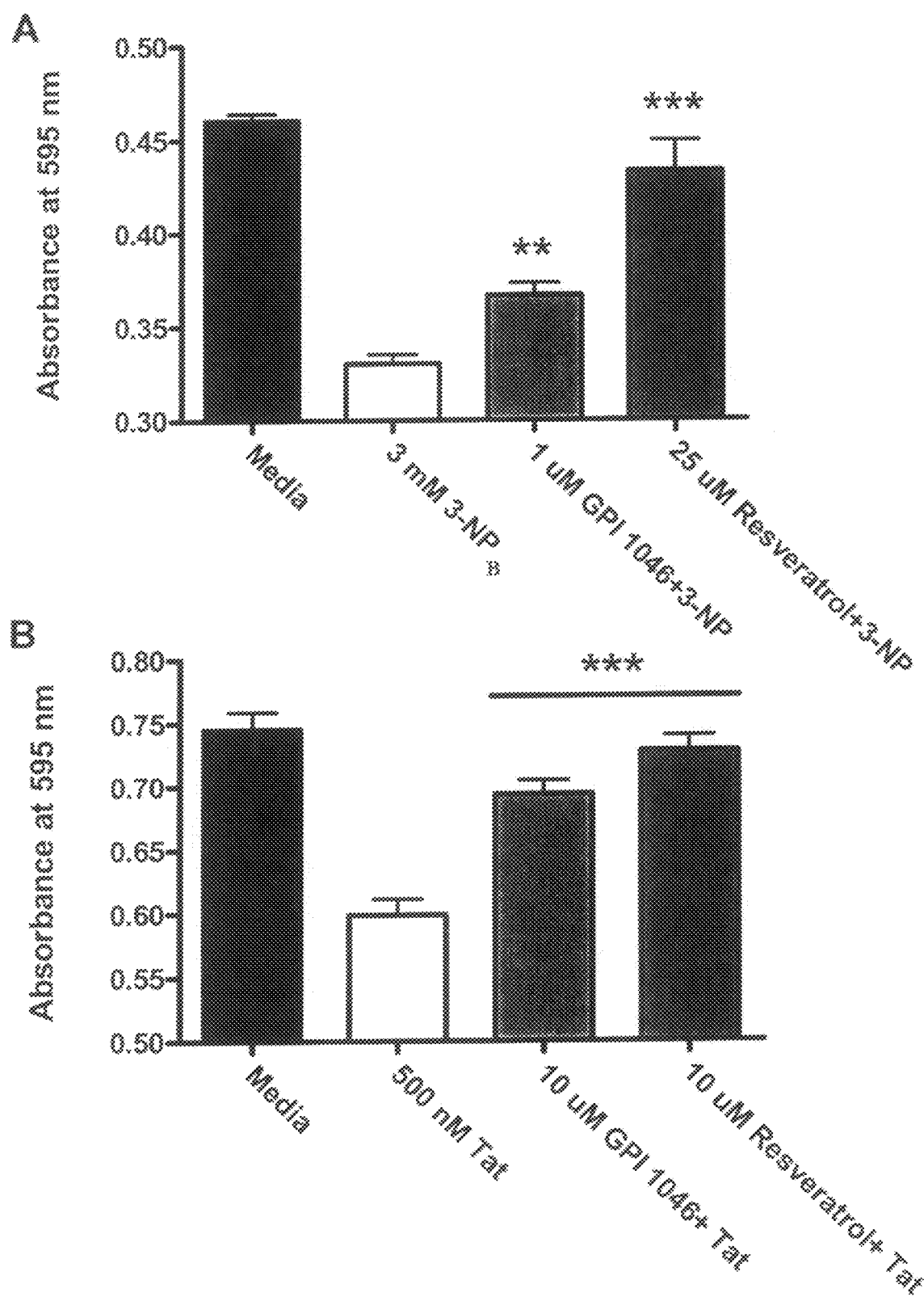
FIG. 4 is a set of bar graphs showing the results of an MTT viability assay of mixed hippocampal cell cultures in which (A) the effect of 3-NP (3 mM) is tested alone or in the presence of neuroprotective antioxidants GPI 1046 (1 μM) or Resveratrol (25 μM); and (B) the effect of HIV Tat protein (500 nM) is tested alone or in the presence GPI 1046 (10 μM) or Resveratrol (10 μM). The statistical significance of data compared to either 3-NP or Tat treatment (right panel) is indicated by ANOVA, with Newman-Keuls post hoc comparisons.  indicates p<0.01; * indicates p<0.001 (n=8 per treatment). Each experiment was performed in triplicate.

The assay system was validated using two neuroprotective agents, GPI 1046 and Resveratrol. Both of these compounds has demonstrated antioxidant and/or neuroprotective activities in numerous in vitro and in vivo assays (for review, see Poulter et al. (2004), *Neuroscience*, 128(1):1-6; Caporello, et al. (2006), *J Neurochem*, 98(1): 146-155; Zamin et al. (2006), *Neurobiol Dis*, 24(1):176-182). Cultures were preincubated with GPI 1046 or Resveratrol for one hour prior to an 18 hour exposure to 3 mM 3-NP. These "positive control" neuroprotective compounds significantly protected rat neurons from oxidative damage elicited by 3-NP (FIG. 4A) in the rat mixed hippocampal culture assay system described above. The same neuroprotective compounds were evaluated for efficacy against HIV-1 Tat protein toxicity using the same 1 hour preincubation protocol. As with the 3-NP neurotoxicity assay, these compounds protected hippocampal neurons from Tat toxicity as well (FIG. 4B). These data indicated that the measurement of neuroprotection against 3-NP toxicity likely serves as a good indicator of protective activity against HIV-1 Tat toxicity.

Using the validated 3 mM 3-NP neurotoxicity assay described above, we evaluated the neuroprotective efficacy of approximately 2000 compounds from the Spectrum Collection (MicroSource Discovery) as described in Example 1. Several of the neuroprotective compounds identified in this collection were modified terpenoids. Thus, we tested an expanded collection of modified terpenoids in the in vitro neuroprotection assay. As shown in Tables 2 and 3, a number of modified terpenoid compounds were identified as having neuroprotective activity against 3-NP.

Figure 5:
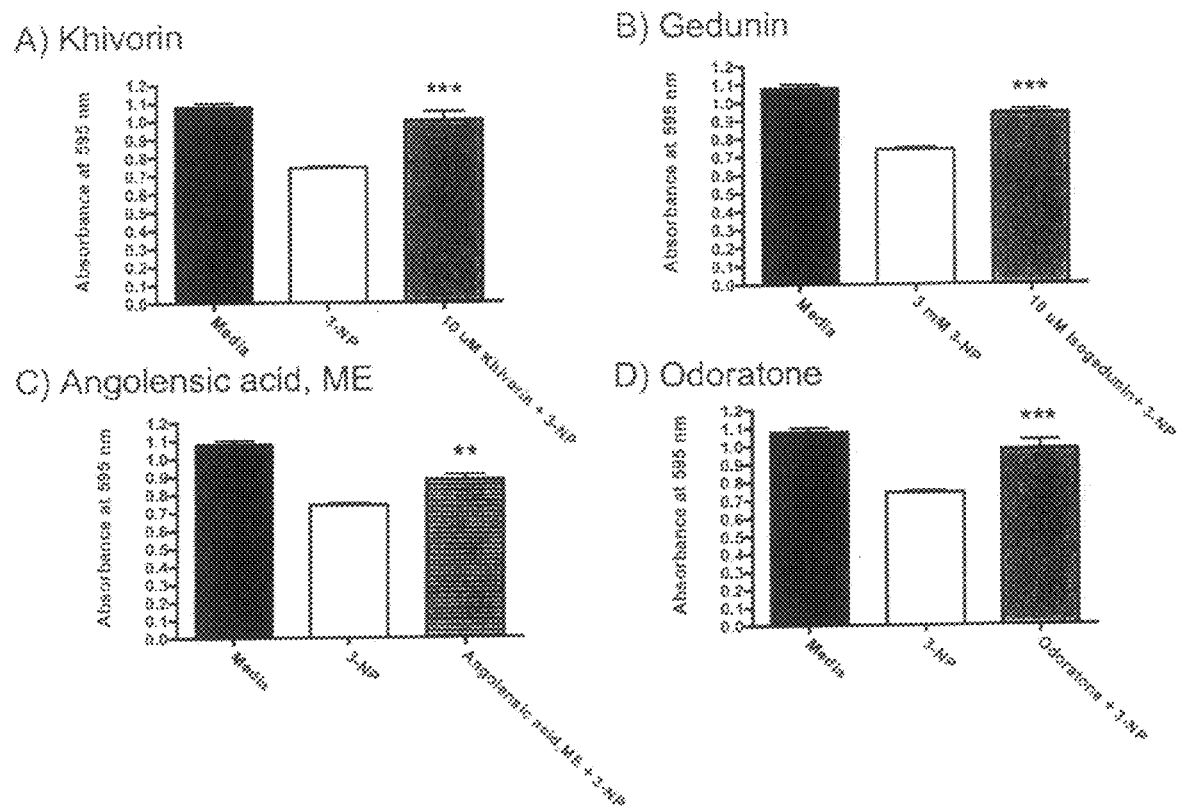
FIG. 5 is a set of bar graphs showing the results of an MTT viability assay of mixed hippocampal cell cultures in which the effect of 3-NP (3 mM) is tested alone or in the presence of (A) Khivorin (10 μM); (B) Isogedunin (10 μM); (C) Angolensic acid, ME; and (D) Odoratone. The statistical significance of data compared to 3-NP treatment is indicated by ANOVA, with Newman-Keuls post hoc comparisons.  indicates p<0.01; * indicates p<0.001.
Figure 6:
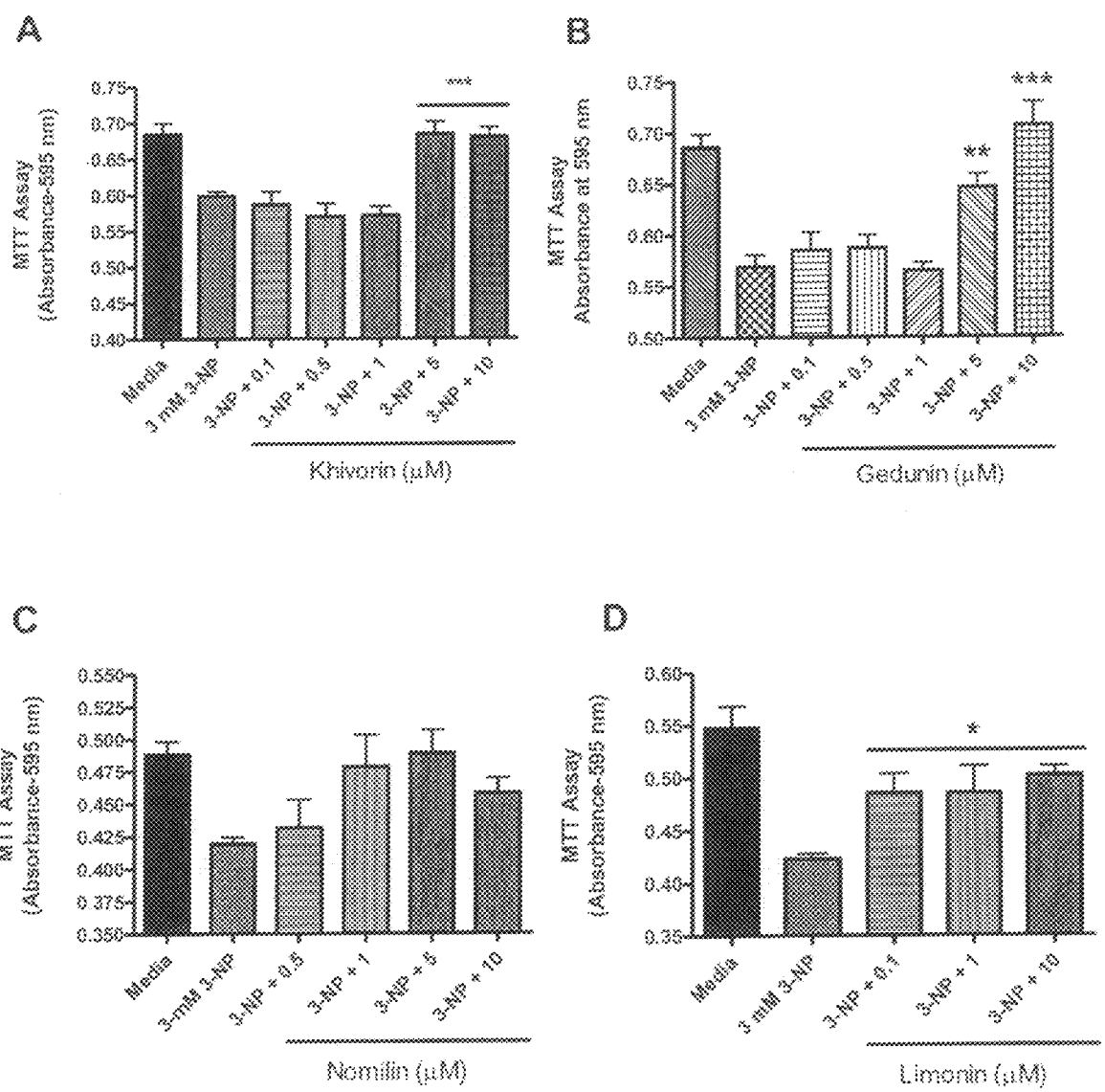
FIG. 6 is a set of bar graphs showing the results of an MTT viability assay of mixed hippocampal cell cultures in which the effect of 3-NP (3 mM) is tested alone or in the presence of a range of concentrations of modified terpenoid compounds (A) Khivorin (0.1-10 KM); (B) Isogedunin (0.1-10 μM); (C) Nomilin (0.5-10 μM); and (D) Limonin (0.1-10 μM).

3-NP assay data for four of these compounds are shown in FIG. 5. These compounds protected the mixed hippocampal cultures significantly, with nearly complete protection provided by 10 µM of Khivorin, about 60-70% protection resulting from odoratone, and about 50% protection from gedunin and angolensic acid, methyl ester treatment. The 3-NP protection dose-response characteristics of the modified terpenoids Khivorin, Gedunin, Nomilin, and Limonin are shown in FIGS. 6A-6D, respectively.

Figure 7:
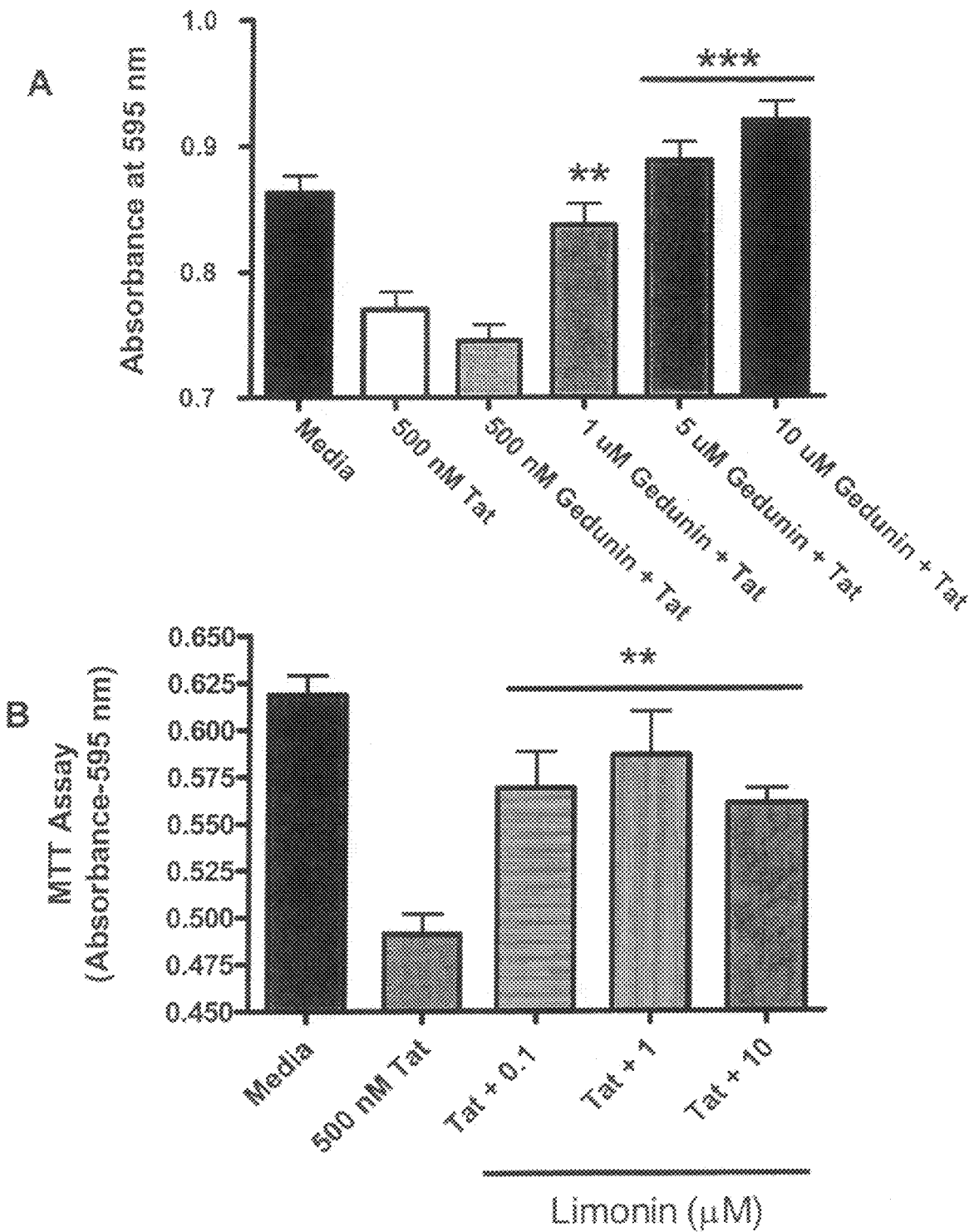
FIG. 7 is a set of bar graphs showing the results of an MTT viability assay of mixed hippocampal cell cultures in which the effect of the neurotoxic HIV Tat protein (500 nM) is tested alone or in the presence of a series of concentrations of (A) Isogedunin (0.5-10 μM) and (B) Limonin (0.1-10 μM).

Gedunin and Limonin also dose dependently protected hippocampal cultures from HIV-1 Tat toxicity (FIG. 7), with nearly complete neuroprotection provided by 1-10 µM Gedunin. Thus, some modified terpenoids also protect hippocampal neurons from HIV-1 neurotoxic protein degeneration.

Figure 8:
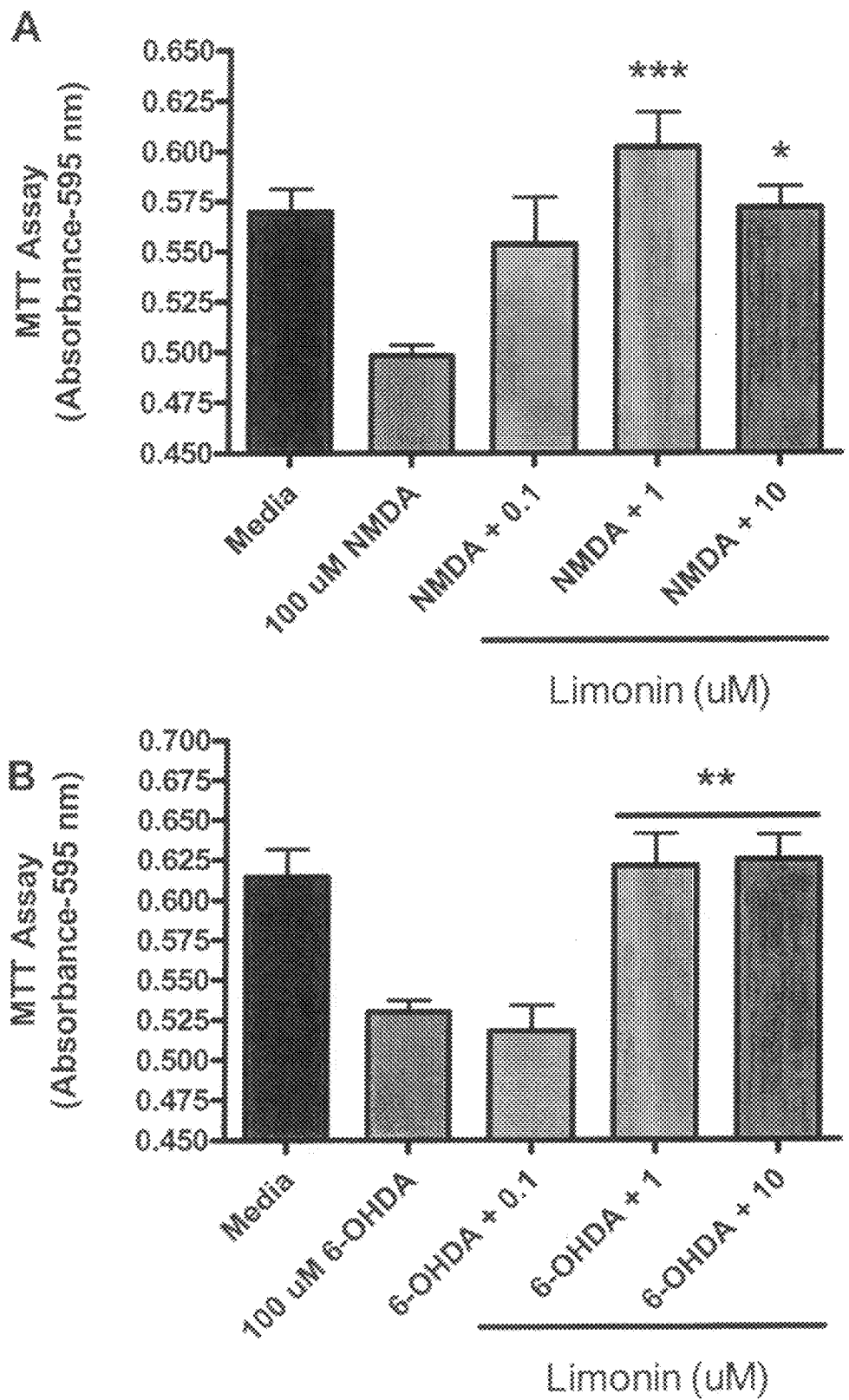
FIG. 8 is a set of bar graphs showing the results of an MTT viability assay of mixed hippocampal cell cultures in which the effect of (A) NMDA (100 μM) or (B) 6-OHDA (100 μM) is tested alone or in the presence of a range of concentrations of Limonin (0.1-10 μM).

We also tested the ability of Limonin to protect against N-methyl-D-Aspartic Acid (NMDA) excitotoxicity, and 6-Hydroxydopamine (6-0HDA), a dopaminergic neurotoxin. As shown in FIG. 8, Limonin dose-dependently blocked the neurotoxicity of both NMDA (FIG. 8A) and 6-OHDA (FIG. 8B) conferring complete protection at the highest Limonin dose tested (10 µM).

Figure 9:
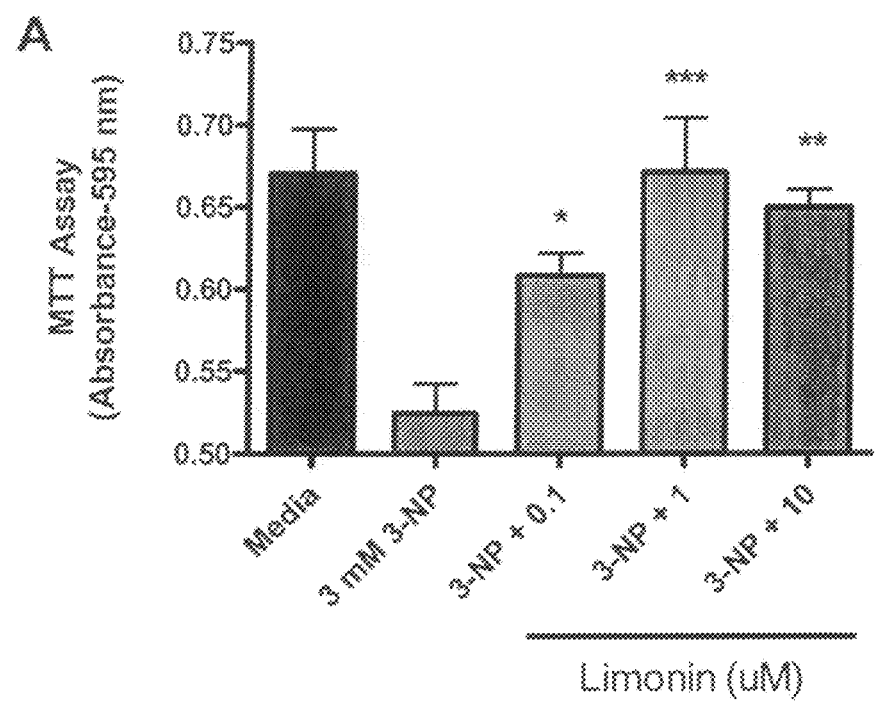
FIG. 9 is a set of bar graphs showing the results of an MTT viability assay of human fetal neuron cultures in which the effect of (A) 3-NP (3 mM) or (B) 6-OHDA (100 μM) is tested alone or in the presence of a range of concentrations of Limonin (0.1-10 μM).
Figure 9:
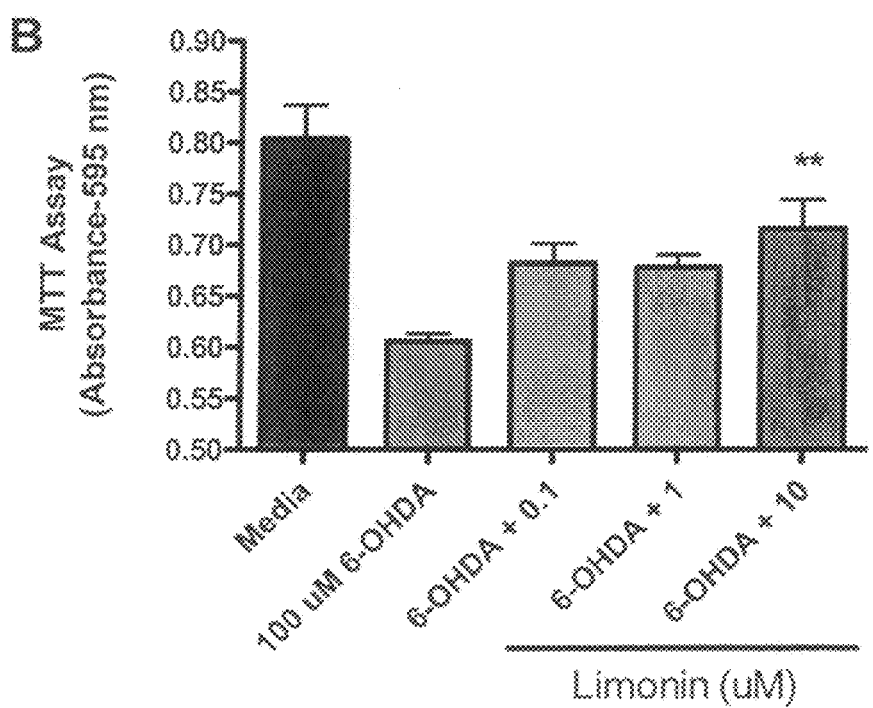

Finally, we sought to determine if the compounds tested in rat neuronal cultures would also be effective on cultured human fetal neurons. Indeed, as shown in FIG. 9, Limonin dose-dependently protected human fetal neuronal cultures against both 3-NP (FIG. 9A) and 6-OHDA.

Based on these data, we concluded that various modified terpenoid compounds are neuroprotective.

| Compound | Structure | % Protection |
|---|---|---|
| 3alpha-ACETOXYDIHYDRODEOXY-GEDUNIN | 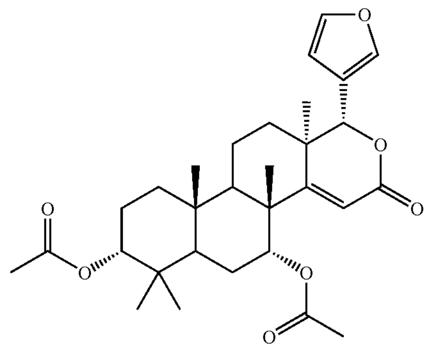 | 151 |
| 1,3-DIDEACETYLKHIVORIN | 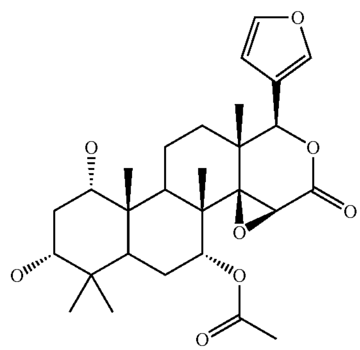 | 129 |
| DEOXODIHYDROGEDUNIN | 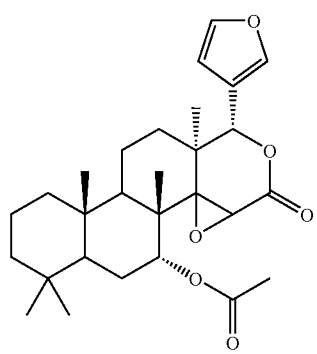 | 101 |
| 3beta-ACETOXYDEOXYANGOLENSIC ACID, METHYL ESTER | 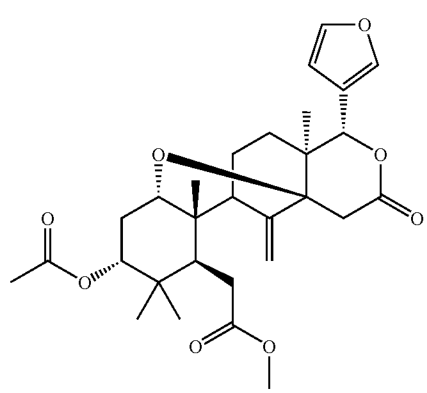 [SMILES: C=C1C2CC[C@@]3(C)[C@H](c4ccoc4)OC(=O)C[C@]13O[C@H]1C[C@@H](OC(C)=O)C(C)(C)[C@H](CC(=O)OC)[C@@]21C] | 128 |

| Compound | Structure | % Protection |
|---|---|---|
| TRIDESACETOXYKHIVORIN | 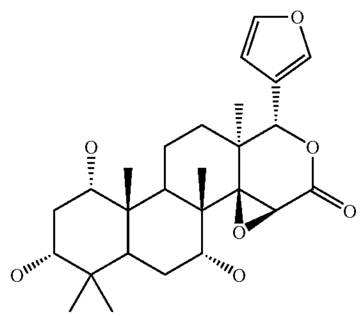 | 97 |
| 7beta-HYDROXY-7-DESACETOXYKHIVORINIC ACID, METHYL ESTER | 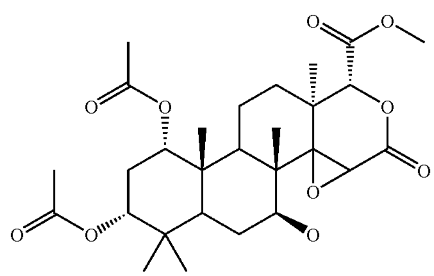 | 84 |
| 3beta-HYDROXYDEOXODIHYDRO-GEDUNIN | 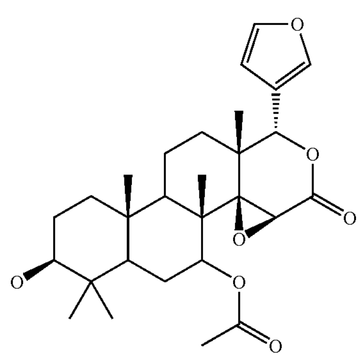 | 82 |
| DEOXODEOXYDIHYDRO-GEDUNIN | 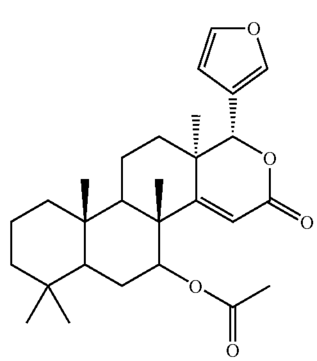 | 77 |

-continued

| Compound | Structure | % Protection |
|---|---|---|
| KHIVORIN | 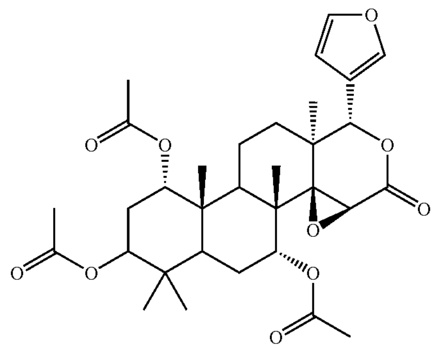 | 70 |
| EPOXYGEDUNIN | 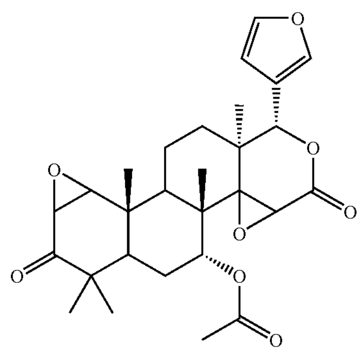 | 69 |
| 7-EPIKHIVORIN | 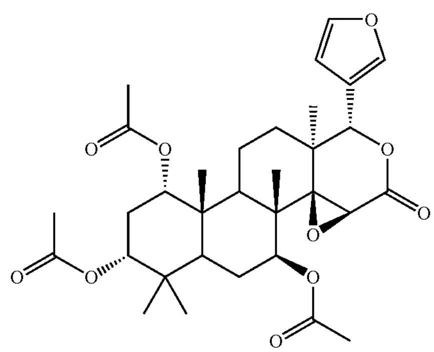 | 65 |
| 3beta,7beta-DIACETOXYDEOXODEACETOXY-DEOXYDIHYDROGEDUNIN | 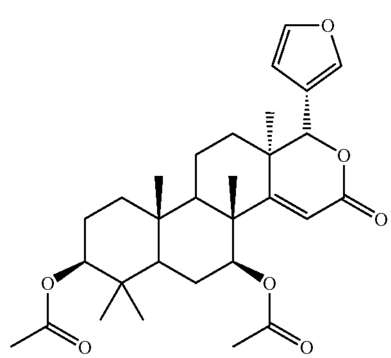 | 61 |

-continued

| Compound | Structure | % Protection |
|---|---|---|
| DESACETYL (7)KHIVORINIC ACID, METHYL ESTER | 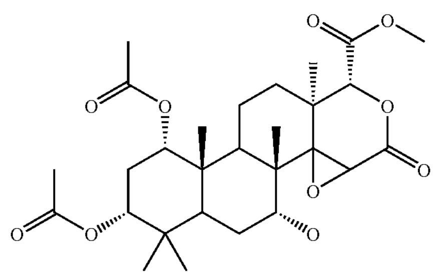 | 58 |
| 3-DEOXO-3beta-ACETOXYDEOXYDIHYDRO-GEDUNIN | 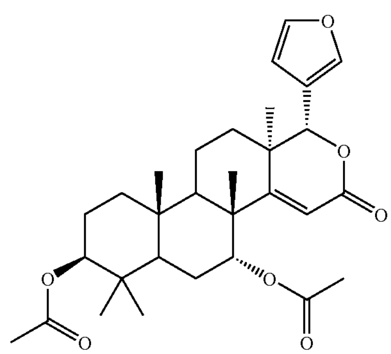 | 56 |
| 3beta-HYDROXYDEOXODIHYDRO-DEOXYGEDUNIN | 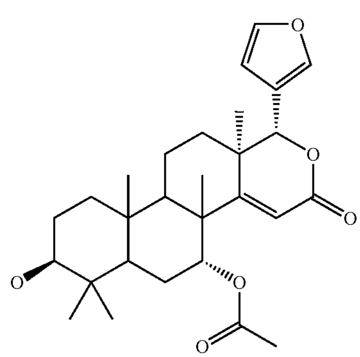 | 56 |
| DEOXYGEDUNOL ACETATE | 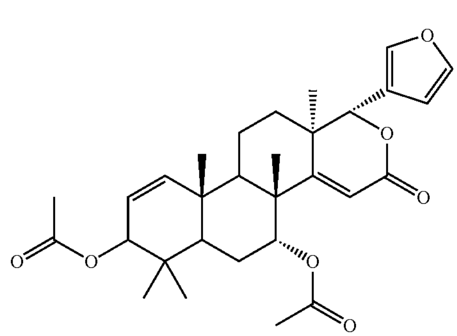 | 54 |

| Compound | Structure | % Protection |
|---|---|---|
| ISOGEDUNIN | 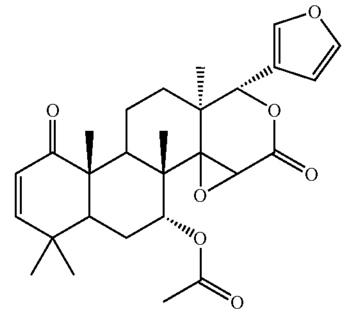 | 50 |
| GEDUNOL | 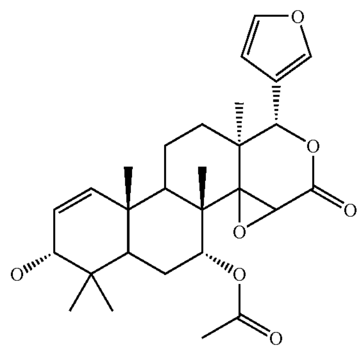 | 45 |
| 2,3-DIHYDROISOGEDUNIN | 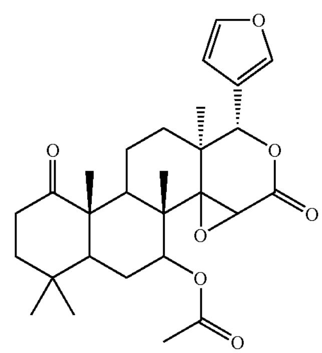 | 44 |
| 7-DEACETOXY-7-OXO-KHIVORINIC ACID, METHYL ESTER | 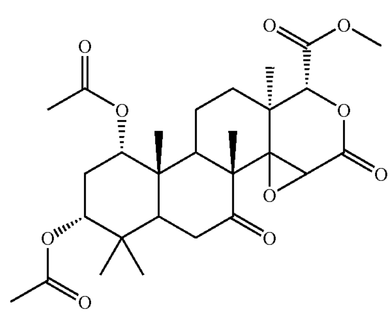 | 42 |

| Compound | Structure | % Protection |
|---|---|---|
| TRIDESACETOXYKHIVORIN | 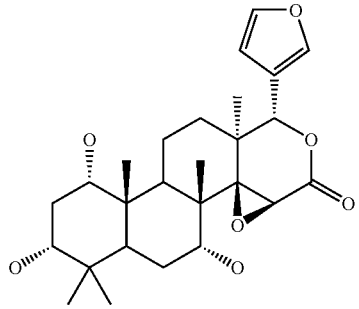 | 39 |
| 3beta-ACETOXYDEOXODIHYDRO-GEDUNIN | 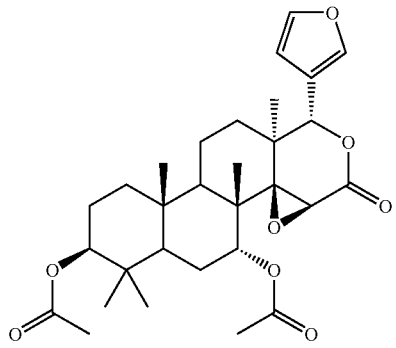 | 39 |
| DEACETOXY-7-OXOGEDUNIN | 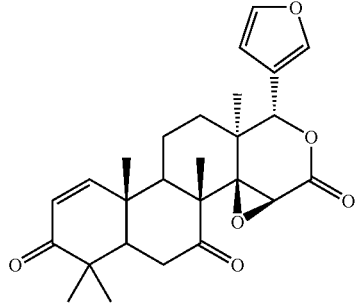 | 38 |
| DEOXYKHIVORIN | 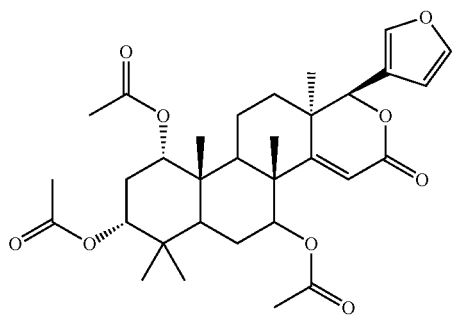 | 36 |

-continued

| Compound | Structure | % Protection |
|---|---|---|
| 7-DEACETOXY-7-OXOKHIVORIN | 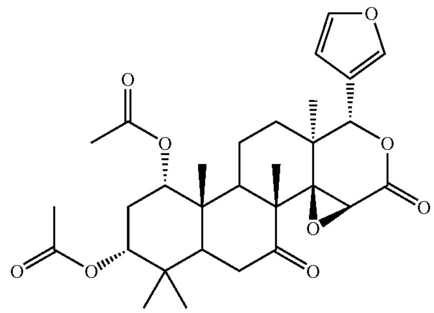 | 36 |
| 3alpha-HYDROXY-3-DEOXYANGOLENSIC ACID METHYL ESTER | 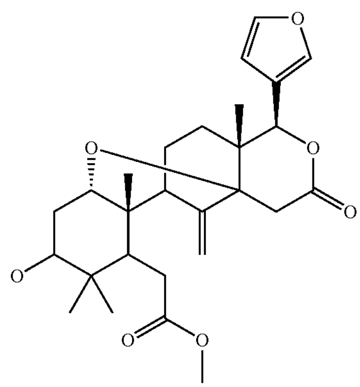 [SMILES: C=C1C2CC[C@]3(C)[C@@H](c4ccoc4)OC(=O)CC13O[C@H]1CC(O)C(C)(C)C(CC(=O)OC)[C@@]21C] | 35 |
| ANGOLENSIC ACID, METHYL ESTER | 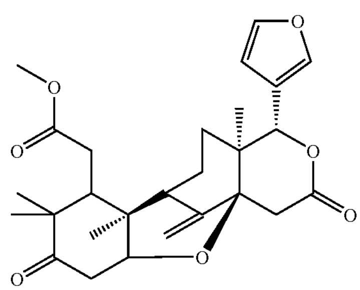 | 33 |
| 7-DEACETYLKHIVORIN | 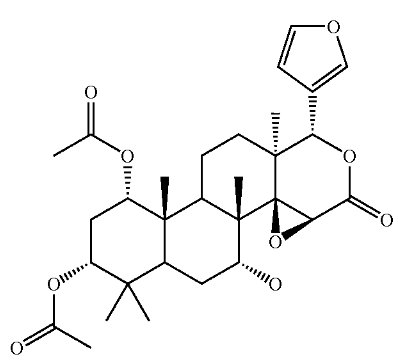 | 32 |

-continued

| Compound | Structure | % Protection |
|---|---|---|
| 3beta-HYDROXYDEOXYDESACETOXY-7-OXOGEDUNIN | 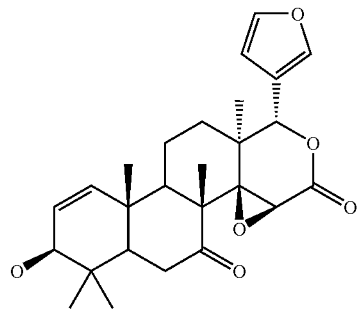 | 30 |
| 3-alpha-HYDROXYDEOXYGEDININ | 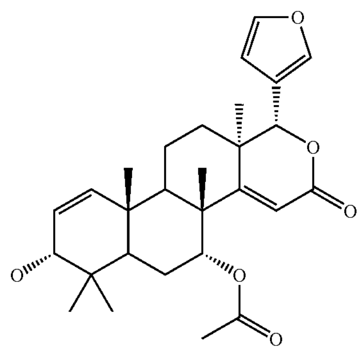 | 28 |
| DIHYDROGEDUNIN | 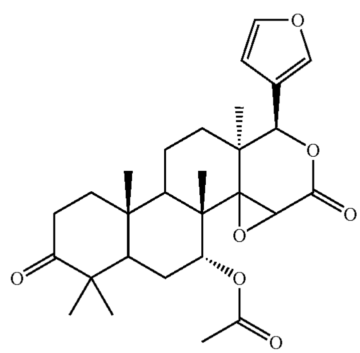 | 28 |
| 6-HYDROXYANGOLENSIC ACID METHYL ESTER | 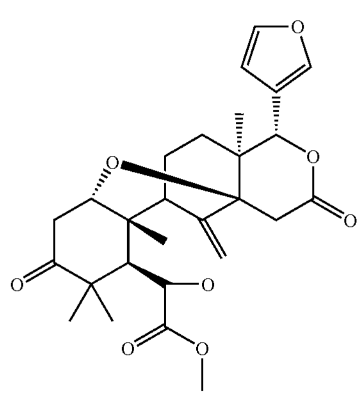 [SMILES: C=C1C2CC[C@@]3(C)[C@H](c4ccoc4)OC(=O)C[C@]13O[C@H]1CC(=O)C(C)(C)[C@H](C(O)C(=O)OC)[C@@]21C] | 26 |

| Compound | Structure | % Protection |
|---|---|---|
| 1,2alpha-EPOXYDEACETOXYDIHYDRO GEDUNIN | 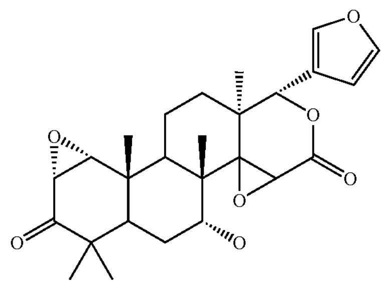 | 25 |
| 7-DEACETOXY-7-OXODEOXYGEDUNIN | 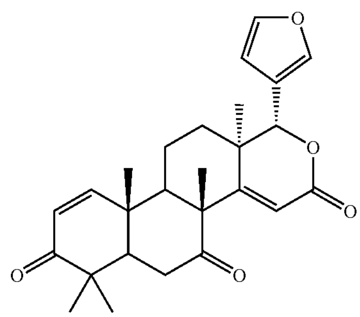 | 24 |
| DEOXYGEDUNIN | 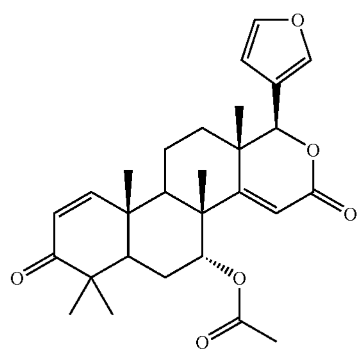 | 23 |
| GEDUNIN | 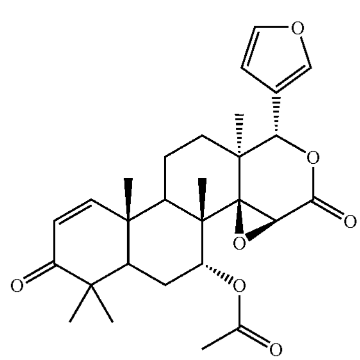 | 40 |

| Compound | Structure | % Protection |
|---|---|---|
| DEACETYLGEDUNIN | 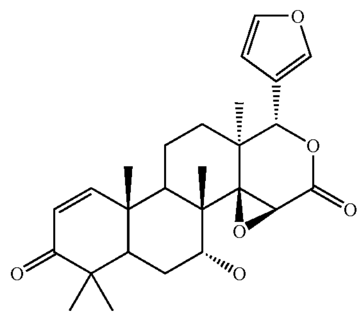 | 19 |
| DIHYDROGEDUNIN ETHANEDITHIOKETAL | 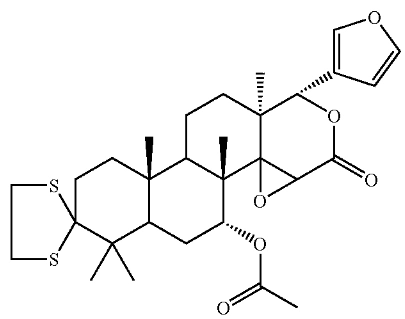 | 19 |
| 1,7-DIDEACETOXY-1,7-DIOXO-3-DEACETLYKHIVORN | 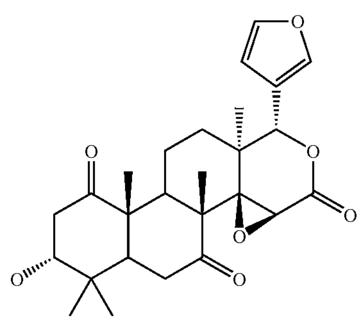 | 15 |
| 1,3-DIDEACETYL-7-DEACETOXY-7-OXOKHIVORIN | 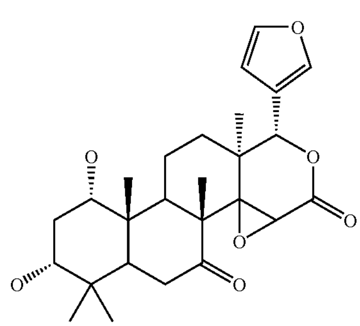 | 15 |

-continued

| Compound | Structure | % Protection |
|---|---|---|
| 1 (2)alpha-EPOXYDEOXYDIHYDRO-GEDUNIN | 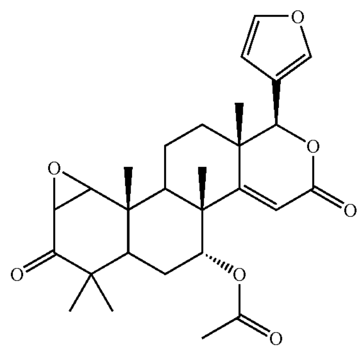 | 14 |

TABLE 3

Modified Terpenoids Exhibiting Neuroprotective Activity against 3-NP

| Structure | % Protection vs 3-NP |
|---|---|
| 3beta-ACETOXYDEOXODIHYDROGEDUNIN | 39 |
| CARAPIN-8(9)-ENE | 38 |
| DEACETOXY-7-OXOGEDUNIN | 38 |
| KHAYANTHONE | 36 |
| DEOXYKHIVORIN | 36 |
| 7-DEACETOXY-7-OXOKHIVORIN | 36 |
| ANGOLENSIC ACID, METHYL ESTER | 33 |
| 7-DEACETYLKHIVORIN | 32 |
| FISSINOLIDE | 28 |
| 6-HYDROXYANGOLENSIC ACID METHYL ESTER | 26 |
| DEOXYGEDUNIN | 23 |
| DEACETYLGEDUNIN | 19 |
| BUSSEIN | 18 |
| CARAPIN | 18 |
| ENTANDROPHRAGMIN | 18 |
| UTILIN | 16 |
| 1,3-DIDEACETYL-7-DEACETOXY-7-OXOKHIVORIN | 15 |
| 1,7-DIDEACETOXY-1,7-DIOXO-3-DEACETYLKHIVORIN | 15 |
| KHAYASIN C | 13 |
| DIHYDROFISSINOLIDE | 12 |
| 8beta-HYDROXYCARAPIN, 3,8-HEMIACETAL | 9 |
| MEXICANOLIDE | 9 |
| QUASSIN | 8 |
| 3-DEACETYLKHIVORIN | 7 |
| PRIEURIANIN | 6 |

Example 3B

In Vitro Modeling of Blood Brain Barrier Permeability to Test Compounds

In vitro models of the Blood Brain Barrier from human brain microvascular endothelial cells (HBMEC) that were isolated and characterized have been published previously (see, e.g., Stins et al. (1997), *J Neuroimmunol*, 76(1-2):81-90; Cucullo et al. (2007), *Epilepsia*, 48(3):505-516). These HBMEC possess gamma glutamyl transpeptidase (GGTP) and drug transporter P-glycoprotein, and junctional proteins as seen by ZO1 immuno-staining, thereby demonstrating their brain endothelial cell characteristics. In vitro BBB models were constructed by growing HBMEC on microporous membranes (0.4 μm pore size) in the upper compartment of semipermeable Transwell™ tissue culture inserts (24 wells, Corning-Costar). The upper compartment compares to blood side and bottom compartment to brain side. Transmission electron microscopy revealed a smooth endothelial cell monolayer, typical rod shaped Weibel-Palade bodies and tight junctions. Polarity was shown after treatment with TNF-α, which resulted in an apical expression of ICAM-1, which is in agreement with data of Wong et al. (1992), *J Neuroimmunol*, 39(1-2):11-21. The presence of junctional proteins is seen by ZO1 immuno-staining and Western blotting for ZO-1, beta-catenin and occludin-1, showing that HBMEC possess endothelial and brain characteristics and functions.

Propidium iodide (PI) (MW=600) at 0.5 mg/ml, an indicator of in vitro blood brain barrier ("BBB") integrity, is applied to the upper compartment along with a vehicle solution or a solution containing test compound at a concentration of 1 μM. At 2 and 4 hours post drug treatment, levels of compound are measured in top and bottom compartments by mass spectrometery as described in Tian et al. (2004), *Rapid Comm Mass Spec*, 18:3099-3104. The level of test compound detected in the bottom compartment is then normalized for differences in PI permeability between the test compound solution and the vehicle control solution.

Example 3C

In Vivo Assessment of Neuroprotective Modified Terpenoid Compounds in a 3-NP-Induced Neurotoxicity Animal Model In order to determine the in vivo efficacy of compounds identified as neuroprotective against 3-NP in vitro, as described herein, we employ a 3-NP-induced neurotoxicity model in rats. See, e.g., Kumar et al. (2006), *Behav Pharmacol*, 17(5-6):485-492.

To induce 3-NP neurotoxicity in vivo, 12-week-old male Lewis rats weighing 340-370 gm are administered intraperitoneal injections of 3-NP (20 mg/kg) for 4 days. The animals are divided into three treatment groups (n=12 per group) as follows:

Group 1 is administered Khivorin, Gedunin, Odoratone, Angolensic acid, or another modified terpenoid compound once daily (10 mg/kg; oral gavage) beginning four days prior to and continuing for four days subsequent to the beginning of the 3-NP injections.

Group 2 is administered saline vehicle (negative control), by oral gavage, beginning four days prior to and continuing for four days subsequent to the beginning of the 3-NP injections.

Group 3 is administered resveratrol (positive control) (10 mg/kg; oral gavage) by oral gavage, beginning four days prior to and continuing for four days subsequent to the beginning of the 3-NP injections.

Subsequent to the beginning of the 3-NP injections, animals are assessed for significant loss of body weight, a decline in motor function (locomotor activity, movement pattern, and vacuous chewing movements) and cognitive deficits (e.g., impairment in learning or memory). Differences of performance between groups are analyzed at each time point by two-tailed t test.

Twenty-four hours after the last 3-NP injection animals are anesthetized, perfused transcardially with saline, followed by ice-cold 4% paraformaldehyde in 0.1 M phosphate buffer, pH 7.4. Brains are immediately removed and postfixed overnight in the same fixative and then cryoprotected in 30% sucrose in 0.1 M phosphate buffer, pH 7.4. Sequential coronal sections (30 μm) are made on a freezing microtome, starting from the anterior aspect of the corpus callosum throughout the entire striatum. For histological assessment, every sixth section (210 μm interval) is processed for cresyl violet staining to assess cell loss and neuronal degeneration. Cresyl violet staining is performed with standard protocols.

Stereological analysis of lesion volumes are performed by digitally acquiring cresyl violet-stained sections through the striatum at 4× objective using a computerized image analysis system. Lesion volumes for each group of animals are calculated by summing the cross-sectional areas of the lesion in each section and multiplying this value by the distance between sections.

Compounds found to confer a significant reduction in 3-NP-induced behavioral deficits or neuroanatomical lesion volume are considered to be neuroprotective in vivo.

Example 3D

In Vivo Assessment of Identified Neuroprotective Compounds in a Focal Ischemia Animal Model A problem with ongoing methodology used to test the efficacy of neuroprotective compounds in vivo in the classic Experimental Autoimmune Encephalomyelitis (EAE) model is that inflammation-mediated lesions are randomly distributed within the central nervous system, thereby making uniform quantification of axonal damage and neuronal cell death difficult. In contrast, a focal lesion model induces a localized inflammatory response and subsequent lesion only within a specific region of the spinal cord. The focal lesion model therefore enables a more accurate assessment of the efficacy of neuroprotective agents because a specific region of the spinal cord and brain are compared between animals. Furthermore, the focal lesion model decreases variability found within the classic EAE models and therefore decreases the number of animals required.

Lewis rats (12-15 rats per treatment group) are treated with a test compound at a dose of 0.1, 1, and 10 mg/kg s.c or p.o. or with vehicle once daily for 3 days prior to immunization with MOG and incomplete Freunds Adjuvant as described below. Eighteen days later, the animals are subjected to laminectomy of the dorsal column at T8 and injected with TNF-α and γ-IFN to induce a focal EAE lesion as described below. Three weeks later, the animals are sacrificed. Outcome measures include behavioral studies (Basso-Beattie-Bresnahan scale), evoked potentials (nerve conduction velocity), radiological outcomes (Diffusion Tensor Imaging, Magnetic Resonance Imaging), and histology measurements (Luxol Fast Blue, Toluidine Blue, Myelin Basic Protein, phospho-Neurofilament and Axonal degeneration). A second cohort includes another set of animals where the same drug regimen listed above is initiated following the laminectomy.

Animals

For these experiments, Lewis rats (10-12 weeks old) are allowed free access to food and water to acclimate 7-10 days before the initiation of experiments. At the time of the study, the animals weigh 200-250 g.

Induction of Myelin Oligodendrocyte Glycoprotein (MOG) Sensitivity

Animals are injected subcutaneously at the base of the tail with 100 μl of recombinant $MOG_{1-125}$ (250-500 μg/mL) emulsified in incomplete Freund's adjuvant. No manipulations are performed for 18-30 days after immunization to allow for the immune system to develop a sensitivity to MOG. This procedure does not induce clinical symptoms of EAE.

Induction of Focal EAE Lesion

To induce an EAE lesion within a specific region of the spinal cord, a steriotaxic injection of TNF-α and IFN-γ is administered within the spinal cord after laminectomy. The animals are shaved prior to initiation of the procedure. Anesthetized animals are placed in the prone position, and a midline incision is made. Following the dissection of fascia and muscle, a laminectomy is performed at T8 with Rongeur forceps. A focal EAE lesion within the cortical spinal tract is induced by administering 2 μL of 250 ng of TNF-α and 150 Units of IFN-γ dissolved in phosphate buffered saline with trace amounts of Monastral Blue using a capillary glass tube. Following surgery the wound is sutured first through the fascia, and then the skin with a 4.0 vicryl thread or with wound clips. Animals are warmed and allowed to recover.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of inhibiting HIV tat- or gp120-induced toxicity in a neuronal or glial cell in a subject having AIDS-related dementia, comprising administering to the subject a therapeutically effective amount of the pharmaceutical composition comprising

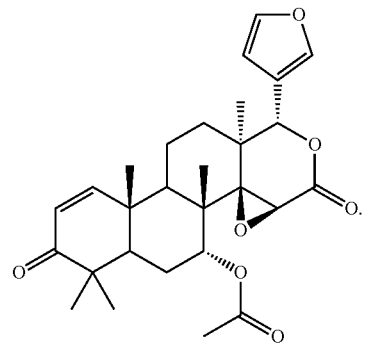

2. A method of inhibiting HIV tat- or gp120-induced toxicity in a neuronal or glial cell in a hippocampal culture, comprising administering 1 to 10 μM of

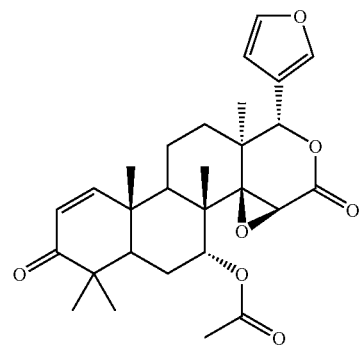
to the culture.
* * * * *